United States Patent
Kobayashi et al.

(10) Patent No.: US 10,539,562 B2
(45) Date of Patent: Jan. 21, 2020

(54) TESTING DEVICE AND METHOD FOR PRODUCING SAME, AND TESTING KIT, TRANSFER MEDIUM FOR TESTING DEVICE, AND TESTING METHOD

(71) Applicants: Rie Kobayashi, Kanagawa (JP); Naoki Shiraishi, Kanagawa (JP)

(72) Inventors: Rie Kobayashi, Kanagawa (JP); Naoki Shiraishi, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 15/844,857

(22) Filed: Dec. 18, 2017

(65) Prior Publication Data

US 2018/0172679 A1 Jun. 21, 2018

(30) Foreign Application Priority Data

Dec. 20, 2016 (JP) .................................. 2016-246769

(51) Int. Cl.
*G01N 33/558* (2006.01)
*G01N 33/545* (2006.01)

(52) U.S. Cl.
CPC .......... *G01N 33/545* (2013.01); *G01N 33/558* (2013.01); *G01N 2333/59* (2013.01)

(58) Field of Classification Search
CPC ............................. G01N 33/545; G01N 33/558
See application file for complete search history.

(56) References Cited

U.S. PATENT DOCUMENTS

| | | | | |
|---|---|---|---|---|
| 5,104,811 A | * | 4/1992 | Berger | ................. G01N 33/525 436/164 |
| 5,420,016 A | * | 5/1995 | Boguslaski | .............. C12Q 1/04 106/2 |
| 2003/0166291 A1 | * | 9/2003 | Jones | ................. G01N 33/5302 436/71 |
| 2010/0159616 A1 | | 6/2010 | Park et al. | |
| 2015/0079668 A1 | | 3/2015 | Kobayashi | |
| 2016/0008812 A1 | | 1/2016 | Kobayashi | |
| 2016/0223535 A1 | | 8/2016 | Kobayashi | |
| 2016/0252504 A1 | | 9/2016 | Kobayashi | |
| 2016/0274100 A1 | | 9/2016 | Kobayashi | |

(Continued)

FOREIGN PATENT DOCUMENTS

| | | |
|---|---|---|
| JP | 2005-010001 | 1/2005 |
| JP | 2016-145789 | 8/2016 |

(Continued)

OTHER PUBLICATIONS

Extended European Search Report dated Apr. 30, 2018 in Patent Application No. 17208463.4.

(Continued)

*Primary Examiner* — Melanie Brown
(74) *Attorney, Agent, or Firm* — Oblon, McClelland, Maier & Neustadt, L.L.P.

(57) ABSTRACT

Provided is a testing device including: a porous flow path member in which a flow path for flowing a sample is formed; and a resin layer provided at at least one position over the flow path member, wherein the resin layer is a porous body formed of a hydrophobic material, and wherein a reagent reactive with the sample is formed as a solid phase over a surface of the resin layer facing the flow path member and inside voids of the resin layer.

10 Claims, 8 Drawing Sheets

(56) References Cited

U.S. PATENT DOCUMENTS

| | | |
|---|---|---|
| 2017/0067892 A1 | 3/2017 | Kobayashi |
| 2017/0176431 A1 | 6/2017 | Hirata et al. |
| 2017/0322202 A1 | 11/2017 | Kobayashi |
| 2018/0224436 A1* | 8/2018 | Edwards ............ G01N 21/8483 |

FOREIGN PATENT DOCUMENTS

| | | |
|---|---|---|
| WO | WO 2007/119991 A1 | 10/2007 |
| WO | WO 2015/041372 A1 | 3/2015 |
| WO | WO 2015/129924 A1 | 9/2015 |

OTHER PUBLICATIONS

Tinglu Yang, et al., "Fabrication of Phospholipid Bilayer-Coated Microchannels for On-Chip Immunoassays", Analytical Chemistry, XP001091759, vol. 73, No. 2, Jan. 15, 2001, pp. 165-169.

Belachew Feyssa, et al., "Patterned Immobilization of Antibodies within Roll-to-Roll Hot Embossed Polymeric Microfluidic Channels", PLOS One, XP055340277, vol. 8, No. 7, Jul. 2013, pp. 1-11.

* cited by examiner

TESTING DEVICE AND METHOD FOR PRODUCING SAME, AND TESTING KIT, TRANSFER MEDIUM FOR TESTING DEVICE, AND TESTING METHOD

CROSS-REFERENCE TO RELATED APPLICATIONS

The present application claims priority under 35 U.S.C. § 119 to Japanese Patent Application No. 2016-246769 filed Dec. 20, 2016. The contents of which are incorporated herein by reference in their entirety.

BACKGROUND OF THE INVENTION

Field of the Invention

The present disclosure relates to a testing device and a method for producing the same, and a testing kit, a transfer medium for a testing device, and a testing method.

Description of the Related Art

Hitherto, as immunoassay methods for detecting and quantifying an antigen or an antibody utilizing a reaction between the antigen and the antibody, testing devices in which flow paths for flowing samples are formed have been used in order to test samples such as blood, DNAs, foods, and beverages.

For example, the testing devices are formed of; a sample pad serving as a liquid receiving portion for receiving a testing liquid; a conjugate pad in which the testing liquid supplied from the sample pad is allowed to undergo a reaction; and a membrane film in which the testing liquid supplied from the conjugate pad flows. In these testing devices, reagents such as capture antibodies are typically immobilized to fiber inside a flow path member. Judgment lines (a test line and a control line), which serve as detecting portions, are formed by directly coating a liquid in which a capture antibody is dissolved over the flow path member, which is formed of a porous material. Therefore, the capture antibody is present inside the porous material diffusively. This leads to problems such as occurrence of unevenness in the density of a labeled antibody accumulated, and blurring of both edges of the lines resulting in unclear color development. Hence, there is proposed a method of immobilizing a reagent to a surface of a resin layer and disposing the immobilized reagent over a flow path member (see, for example, Japanese Unexamined Patent Application Publication No. 2016-145789).

There is also proposed a method of immobilizing a reagent to a porous body formed of a hydrophilic material and disposing the reagent over a flow path member (see, for example, Japanese Unexamined Patent Application Publication No. 2005-010001).

SUMMARY OF THE INVENTION

According to one aspect of the present disclosure, a testing device includes a porous flow path member in which a flow path for flowing a sample is formed, and a resin layer provided at at least one position over the flow path member. The resin layer is a porous body formed of a hydrophobic material. A reagent reactive with the sample is formed as a solid phase over a surface of the resin layer facing the flow path member and inside voids of the resin layer.

DESCRIPTION OF THE EMBODIMENTS (Testing Device)

Figure 1:
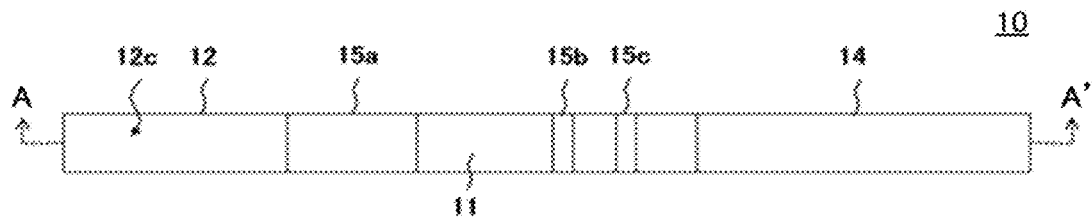
FIG. 1 is a top view illustrating an example of a testing device of the present disclosure.

A testing device of the present disclosure includes a porous flow path member in which a flow path for flowing a sample is formed, and a resin layer provided at at least one position over the flow path member. The resin layer is a porous body formed of a hydrophobic material. A reagent reactive with the sample is formed as a solid phase over a surface of the resin layer facing the flow path member and inside voids of the resin layer.

The testing device of the present disclosure is based on a finding that in existing testing devices, a light scattering-free color developing region that ranges in a direction of thickness to from about 5 micrometers to about 10 micrometers from a surface layer cannot be utilized effectively.

The testing device of the present disclosure is also based on a finding that in existing testing devices, a hydrophilic material used as a porous body that constitutes a resin layer cannot have a reagent (capture antibody) adsorbed sufficiently, so even the use of the porous body as the resin layer cannot lead to a sufficient color developing density at judgment lines (a test line and a control line) serving as the detecting portions.

The present disclosure has an object to provide a testing device including a detecting portion that is uniform and has a high color developing density.

The present disclosure can provide a testing device including a detecting portion that is uniform and has a high color developing density.

The testing device of the present disclosure uses a porous body formed of a hydrophobic material as the resin layer. This enables an antibody to be formed as a high-density solid phase at portions of the porous body contributing to color development, i.e., inside voids present in a direction of thickness and over a surface of the porous body. This makes it possible to obtain judgment lines (a test line and a control line) serving as detecting portions that are uniform and have a high color developing density.

In the testing device, formation of the capture antibody as a solid phase at a side of the resin layer facing the flow path member, as in existing ELISA (Enzyme Linked Immuno Solvent Assay) methods, enables detection of a sample at the resin layer. In the present disclosure, the capture antibody can be formed as a high-density solid phase over a surface of the resin layer and inside voids of the resin layer. This enables detection of a sample with a good sensitivity. Further, in the testing device, a reaction proceeds while a testing liquid that contains the sample is spreading through the flow path member (flow path) and into the voids of the resin layer, being driven by a capillary action, as in existing immunochromato methods. This enables a quick, highly-sensitive measurement, and clear judgment lines (a test line and a control line) that serve as the detecting portions.

The testing device includes a first resin layer and a second resin layer that are provided over the flow path member.

The first resin layer is a porous body formed of a hydrophobic material.

The first resin layer includes at least a capture antibody over a surface of the first resin layer facing the flow path member and inside voids of the first resin layer.

It is preferable that the second resin layer include a labeled antibody over a surface of the second resin layer facing the flow path member.

It is preferable to provide a plurality of first resin layers. To provide a plurality of first resin layers is advantageous because this makes it easy to confirm that the sample is spreading through the flow path member safely.

It is preferable that the first resin layer contain a resin containing a hydrophobic group.

It is preferable that the resin containing a hydrophobic group be any one of a hydrophobic resin and a first amphiphilic resin.

It is preferable that the second resin layer contain a second amphiphilic resin. It is more preferable that the first amphiphilic resin be a resin that contains more hydrophobic groups than the second amphiphilic resin does.

The resin layer and the first resin layer are not particularly limited, may be appropriately selected depending on the intended purpose, and are preferably porous bodies formed of a hydrophobic material.

As the measure of the hydrophobicity, a contact angle between distilled water and the materials constituting the resin layer and the first resin layer can be used. A material having a large contact angle can be considered highly hydrophobic. In this case, a material that can be considered hydrophobic is a material that has a contact angle of 75 degrees or greater with respect to distilled water at room temperature (25 degrees C.), when measured from the coordinates of a liquid droplet image according to an ATAN 1/2θ method and an approaching method that are based on Young equation, which represents a contact angle measurement model the most commonly internationally used in many fields as an equation for calculating a contact angle.

As a method for evaluating the contact angle, for example, there is a method of measuring a contact angle on a surface of a measurement sample that is obtained by smoothing the material constituting the resin layer and the first resin layer (e.g., a porous body, a sheet, and a film) by, for example, heat and pressure. Here, a contact angle is measured by chopping 4.0 microliters of distilled water onto a measurement sample in an environment of 25 degrees C. and −50% RH, using a contact angle meter.

It is preferable that the hydrophobic material be a resin containing a hydrophobic group described below. The hydrophobic group is a group of atoms having a poor intimacy with water or a poor affinity with water and is sparingly soluble in water or sparingly miscible with water.

In the present disclosure, a porous body refers to a structure in which cells are present and the cells are linked together to form a continuous cell. The porous body is distinguished from a non-porous body. The continuous cell is distinguished from independent cells that are not linked together. The continuous cell has a function of sucking in a liquid by a capillary action or letting a gas pass through the continuous cell because the continuous cell has small holes in the walls between the cells. The non-porous body refers to a non-porous structure substantially free of voids, and a structure opposed to a porous material such as a membrane that contains voids provided for promoting absorption of a liquid.

Hence, a material that contains only few cells that have been incidentally mixed in the material during a production process and that do not contribute to promotion of the liquid absorbing action is encompassed within the non-porous body.

The resin layer in the present disclosure is formed of a hydrophobic material. However, because the capture antibody is formed as a solid phase inside the voids of the hydrophobic material, the walls of the cells exhibit hydrophilicity. Hence, the resin layer can allow permeation of the testing liquid into the resin layer by a capillary action that is the same principle as in the flow path member described below, and can allow a reaction with a labeled antibody to occur and develop a color.

The voidage of the resin layer and the first resin layer before formation of a reagent as a solid phase is preferably 10% or higher but 45% or lower. To some extent, the voidage varies from material to material used. However, the voidage is preferably 10% or higher in order to obtain a sufficient color development and is preferably 45% or lower in order for the porous body to maintain a mechanical strength. However, this is non-limiting when a material inherently has a high mechanical strength and can maintain the shape as the porous body even when the voidage is high.

A method for measuring the voidage is not particularly limited and can be selected depending on a measurement sample. Examples of the method include a method of measuring a voidage from a density of a material, and a method of measuring a voidage based on a scanning electron microscopic (SEM) observation of a cross-section of a resin layer and an analysis of the obtained image.

As the method for measuring a voidage from a density, the voidage can be calculated according to a calculation formula 1 below based on a basis weight ($g/m^2$) and an average thickness (micrometer) of the material and the specific gravity of the component of the material.

Voidage (%)={1−[basis weight ($g/m^2$)/average thickness (micrometer)/specific gravity of the component]}×100     [Calculation formula 1]

As the method for measuring a voidage based on an image analysis, there is a method of calculating a voidage based on binarization of image data obtained by observation of a cross-section of a resin layer.

For example, an image analysis using image processing software (IMAGE J) will be described. First, a cross-section of a resin layer is magnified at a magnification of ×5,000 with a scanning electron microscope (SEM) and recorded in the form of a digital image. Next, the image is taken into IMAGE J, and "8 bits" is selected from "Type" of "Image menu". Next, "Threshold" is selected from "Adjust" of "Image menu" likewise, to adjust the threshold such that void regions are extracted from the cross-section of the resin layer to binarize the voids and other regions for distinguishment. Finally, "Analyze Particles" is selected from "Analyze menu", to calculate the area of the voids. Then, the voidage is obtained according to a calculation formula 2 below.

$$\text{Voidage (\%)} = (\text{area of void regions})/(\text{area of whole resin layer}) \times 100 \quad [\text{Calculation formula 2}]$$

The voidage as used herein refers to the average of voidages calculated from 10 arbitrary cross-sectional images.

The average void diameter of the voids of the resin layer and the first resin layer is not particularly limited. The lower limit of the average void diameter has different optimum ranges depending on the particle diameters of gold colloid and fluorescent resin particles to be used on the labeled antibody used, but the lower limit of the average void diameter needs to be 3 times or more greater than the particle diameter of these particles. If the lower limit is less than 3 times greater, the voids may be troubled by, for example, being clogged with the particles, to significantly damage an antigen-antibody reaction inside a test line. The upper limit of the average void diameter is preferably about ⅓ of the average thickness of the resin layer, because a greater void diameter means a smaller surface area of the voids and a smaller amount of the capture antibody that can be formed as a solid phase, leading to a poor effect. For example, the upper limit of the average void diameter is 2 micrometers when the resin layer has an average thickness of 6 micrometers.

Examples of a method for measuring the average void diameter of the voids include a method of measuring the average void diameter based on a scanning electron microscopic (SEM) observation of a cross-section of a resin layer and an image analysis of the obtained image. Specifically, the average void diameter can be obtained according to the same procedure as the image analysis using IMAGE J. When the voids are seen as irregularly formed particles, the average particle diameter of the voids, the average radius of the voids on the longer axis, and the average radius of the voids on the shorter axis can be obtained. The void diameter of the voids as used herein refers to the average particle diameter obtained from distributions on 10 arbitrary cross-sectional images.

A method for forming the voids is not particularly limited and may be appropriately selected depending on the intended purpose. For example, the hydrophobic material may be dispersed in a poor solvent (e.g., water) to be granulated, and then coated over a support and dried to volatilize the solvent. As a result, a resin layer, which is a void-containing aggregation of particles derived from the hydrophobic material can be formed.

The average thickness of the resin layer is not particularly limited, may be appropriately selected depending on the intended purpose, and is preferably 1.0 micrometer or greater in order to obtain a sufficient color developing density, more preferably 1.0 micrometer or greater but 20 micrometers or less in order to effectively utilize a color developing density, and particularly preferably 1.0 micrometer or greater but 10 micrometers or less.

A method for impregnating the voids with a solution containing an antibody (an antibody coating liquid) is not particularly limited and may be appropriately selected depending on the intended purpose. Examples of the method include a pressure impregnation method, a vacuum impregnation method, and a vacuum pressure impregnation method.

The resin layer is formed of a hydrophobic material and the internal walls of the voids exhibit hydrophobicity. Therefore, simply coating the antibody coating liquid cannot allow smooth permeation of the antibody coating liquid into the voids. There is also a case where a gas remaining inside the voids may disturb permeation of the coating liquid. Hence, pressure application after the antibody coating liquid is coated over the resin layer or after the resin layer is impregnated with the antibody coating liquid allows the solution to be pushed into the voids. This makes it possible for the voids to be full of the antibody coating liquid.

The pressure for pressure application is not particularly limited and may be appropriately selected depending on the intended purpose. When the atmospheric pressure is defined as 0, the pressure is preferably 3 MPa or higher and more preferably 3 MPa or higher but 5 MPa or lower for sufficient impregnation with the antibody coating liquid. In principle, a higher pressure is possible. However, as a matter of the device, the pressure of 3 MPa or higher but 5 MPa or lower is tried here.

The time for pressure application can be appropriately selected depending on the intended purpose, and is preferably 10 minutes or longer from a start point of time, which is when the intended pressure is reached. The time for pressure application of 10 minutes or longer is a sufficient time for the antibody coating liquid to reach inside the voids.

The number of times of pressure application can be appropriately selected depending on the intended purpose. When the number of times of pressure application is twice or more (when pressure application is followed by another pressure application with a break in between), the antibody coating liquid gets mixed to supply new antibodies inside the voids, leading to an improved efficiency of formation of the antibody as a solid phase. This step also pushes any bubbles remaining inside the voids to the outside of the voids, to make it easier for the voids to become full of the coating liquid.

Hitherto, judgment lines (a test line and a control line) serving as detecting portions have been commonly formed by directly coating a liquid in which a capture antibody is dissolved over a flow path member formed of a porous material. Hence, the capture antibody diffuses inside the porous material along with permeation of the liquid. However, a color developed by labeling particles such as gold colloid particles to be bound with the capture antibody present inside the porous material cannot actually be sensed due to light scattering. This means that most of the capture antibody is not used effectively. Generally, color developing particles that can be sensed from the porous material are particles that are present at an above the depth of from about 5 micrometers to about 10 micrometers from the surface of the porous material. In order to immobilize the capture antibody needed for detection to this region, there is a need for coating the capture antibody in a large amount considering diffusion of the capture antibody in the direction of thickness. That is, the amount of the capture antibody to be coated increases in proportion to the average thickness of the porous material.

Meanwhile, in the testing device of the present disclosure, a resin layer, which is a porous body including many hydrophobic groups, is used for immobilization of the capture antibody. The resin layer having the capture antibody previously formed as a high-density solid phase over the surface and inside the voids is disposed over the flow path member. Furthermore, the resin layer is adjusted to a thickness that enables a color developed by color developing particles to be sensed, for the sake of efficient utilization of the capture antibody. This enables no wasteful capture antibody to be present in the direction of thickness, leading to an advantage that the amount of the capture antibody to be coated can be suppressed.

Examples of a method for analyzing whether a reagent (antibody) reactive with the sample is formed as a solid phase over the surface of the resin layer facing the flow path member and inside the voids of the resin layer include a quantitative method based on measurement of a fluorescent intensity attributable to the antibody.

First, the resin layer having the antibody formed as a solid phase is shaken in an extraction liquid containing, for example, a surfactant, to extract the antibody from the resin layer.

Next, the fluorescent wavelength of the extraction liquid is measured using a fluorescence spectrophotometer. A fluorescent intensity attributable to the antibody is read from the fluorescent wavelength. The fluorescent intensity is checked against a calibration curve generated separately, to obtain an antibody concentration, which is converted to an amount of the antibody present over and inside the resin layer, to calculate the amount of the antibody formed as a solid phase. For generation of the calibration curve, about 5 levels of solutions with known antibody concentrations are prepared as standard samples. The calibration curve is generated based on fluorescent intensities attributable to the antibody and the antibody concentrations.

Figure 2:
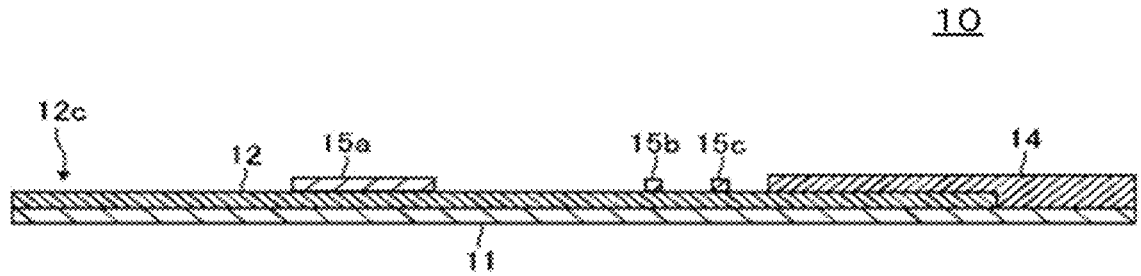
FIG. 2 is a cross-sectional view of the testing device of FIG. 1 taken along A-A'.
Figure 3:
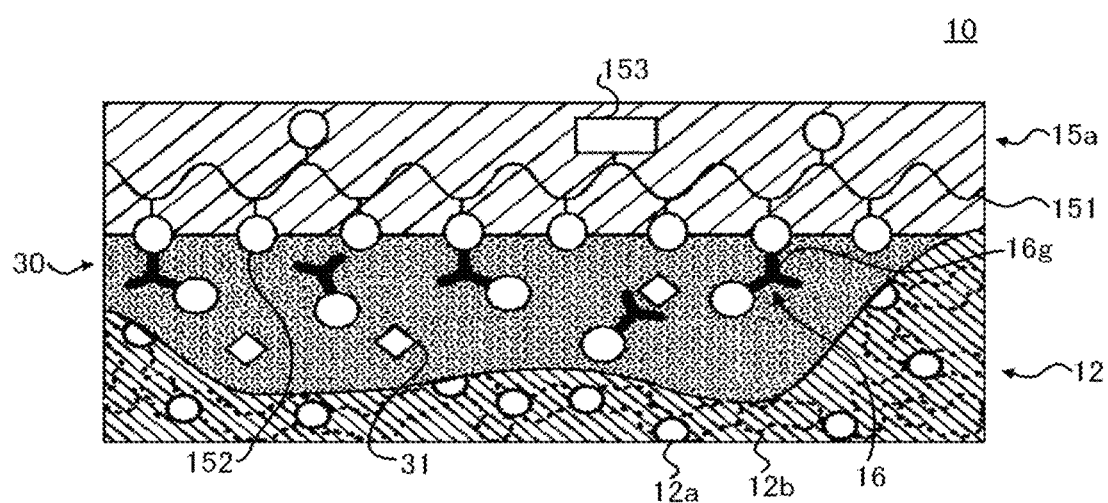
FIG. 3 is a cross-sectional view illustrating an example of a testing device, taken at a portion at which a flow path member and a resin layer face each other.

The testing device of the present disclosure will be described with reference to the drawings. FIG. 1 to FIG. 3, FIG. 4A and FIG. 4B, and the FIG. 5A and FIG. 5B are views illustrating the overall configuration of the testing device. FIG. 1 is a top view illustrating an example of the testing device of the present disclosure. FIG. 2 is a cross-sectional view of the testing device of FIG. 1 taken along A-A'. FIG. 3 is a cross-sectional view illustrating an example of the testing device, taken at a portion at which the flow path member and the resin layer face each other. FIG. 4A to FIG. 5B are cross-sectional views illustrating other examples of the testing device, taken at a portion at which the flow path member and the resin layer face each other.

As illustrated in FIG. 1 to FIG. 5B, the testing device 10 includes a porous flow path member 12 in which a flow path for flowing a hydrophilic testing liquid 30 (an example of a sample), such as blood, spinal fluid, urine, and a sample extraction liquid (e.g., a liquid containing a sample picked with a sample picking unit such as a stick) is formed, and resin layers (15a, 15b, and 15c) provided over the flow path member 12. A labeled antibody 16 reactive with an antigen contained in the testing liquid 30, a capture antibody 17 for capturing the antigen, and a capture antibody (or antigen) 18 for capturing the labeled antibody are formed as solid phases over the surfaces of the resin layers (15a, 15b, and 15c) facing the flow path member 12. This enables the intensity of interaction between the resin layers (15a, 15b, and 15c) and the reagents to be adjusted independently for each of the resin layers (15a, 15b, and 15c). This makes it easy to control release of the labeled antibody 16 and immobilization of the capture antibodies 17 and 18, even when the flow path member 12 is arbitrarily selected depending on the purpose.

A case where in the testing device 10, the flow path member 12 is provided over a base material 11, and an absorbing member 14 is provided over the base material 11 and the flow path member 12 will be described. However, the present disclosure is not limited to this embodiment. What is meant when it is said that something is provided over the flow path member 12 is that that something is provided in a manner to contact the flow path member 12 regardless of which side of the flow path member that something comes to when the testing device 10 is set in place. When an arbitrary resin layer of the resin layers (15a, 15b, and 15c) is to be referred to, the arbitrary resin layer will be denoted as resin layer 15. The capture antibody 18 may be formed as a solid phase by arbitrary chemical binding such as covalent binding, hydrogen binding, and metal binding and arbitrary interaction such as adhesion, cohesion, adsorption, and van der Waals binding. A case where the testing liquid 30 is a hydrophilic testing liquid such as blood, spinal fluid, urine, and a sample extraction liquid (e.g., a liquid containing a sample picked with a sample picking unit such as a stick) will be described below.

As illustrated in FIG. 3, in the testing device 10, the resin layer 15a (second resin layer) contains an amphiphilic resin 151 containing many hydrophilic groups 152.

The content of the hydrophilic groups 152 is preferably 50% by mass or greater of the total amount of the resin layer 15a.

A hydrophilic group is a group of atoms forming a weak bond with water molecules by, for example, hydrogen binding, and having affinity with water. Amphiphilicity means that a substance has affinity with both of water and organic solvents.

The labeled antibody 16 has a hydrophilic portion 16g, by which the labeled antibody 16 is formed as a solid phase over the surface of the resin layer 15a facing the flow path member 12. Meanwhile, when the gap formed at the portion at which the flow path member 12 and the resin layer 15a face each other is filled with the testing liquid 30, the hydrophilic portion 16g of the labeled antibody 16 comes to have affinity with the hydrophilic testing liquid 30 to cause the labeled antibody 16 to be released from the amphiphilic resin 151. When the testing liquid 30 contains an antigen 31, the released labeled antibody 16 and the antigen 31 react and bind with each other by an antigen-antibody reaction. In order to prevent disturbance of binding between the labeled antibody 16 and the antigen 31, it is preferable that the amphiphilic resin 151 be a water-insoluble resin.

Water-insolubility means substantial water-insolubility. Substantial water-insolubility means that a resin undergoes a mass change in an amount of 1% by mass or less when immersed in a large amount of water at 25 degrees C. for 24 hours and then sufficiently dried by a method such as vacuum drying. The reason why the resin undergoes a mass change is that the resin undergoes a mass reduction due to leaching of a by-product (e.g., a monomer component) contained in the resin product into the water.

Figure 4A:
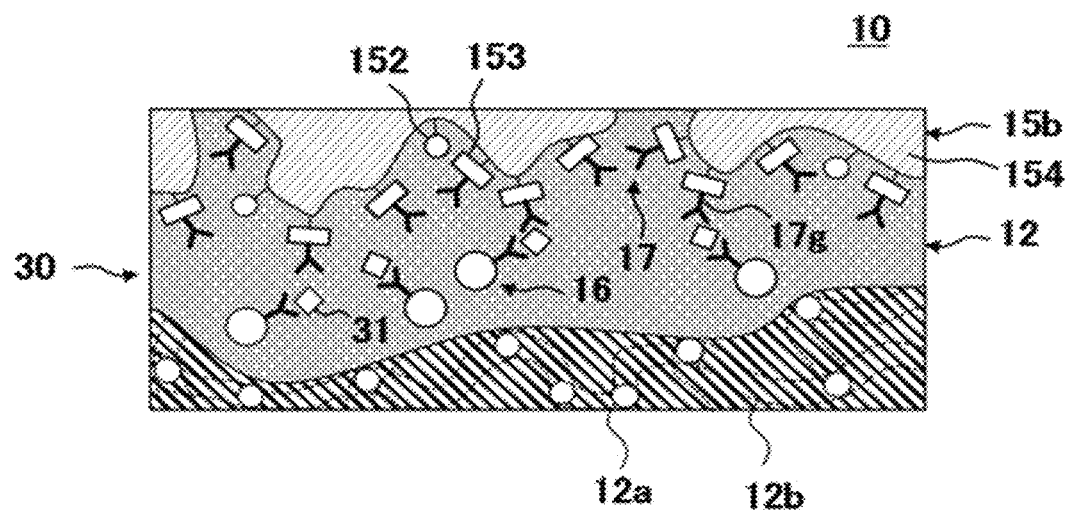
FIG. 4A is a cross-sectional view illustrating another example of a testing device, taken at a portion at which a flow path member and a resin layer face each other.
Figure 4B:
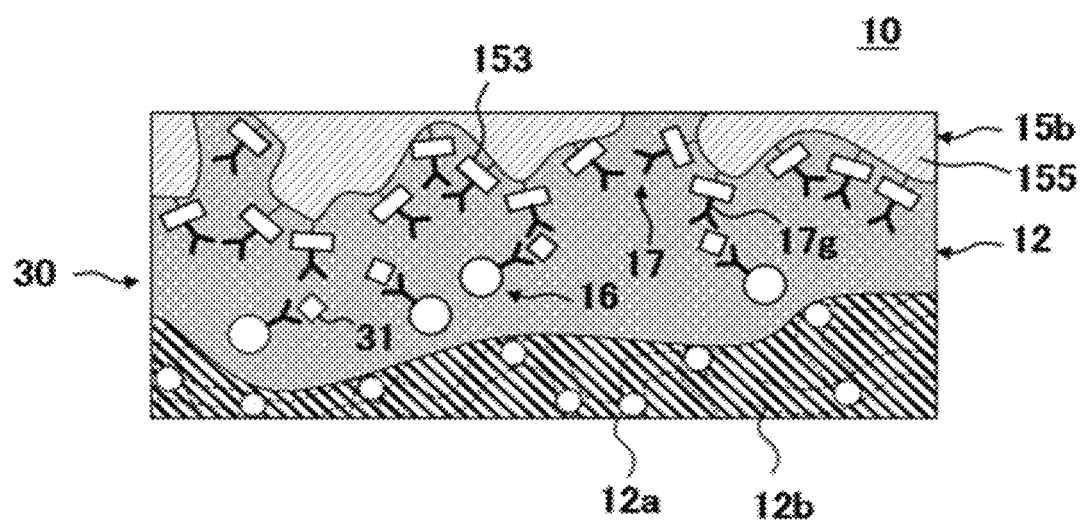
FIG. 4B is a cross-sectional view illustrating another example of a testing device, taken at a portion at which a flow path member and a resin layer face each other.
Figure 5A:
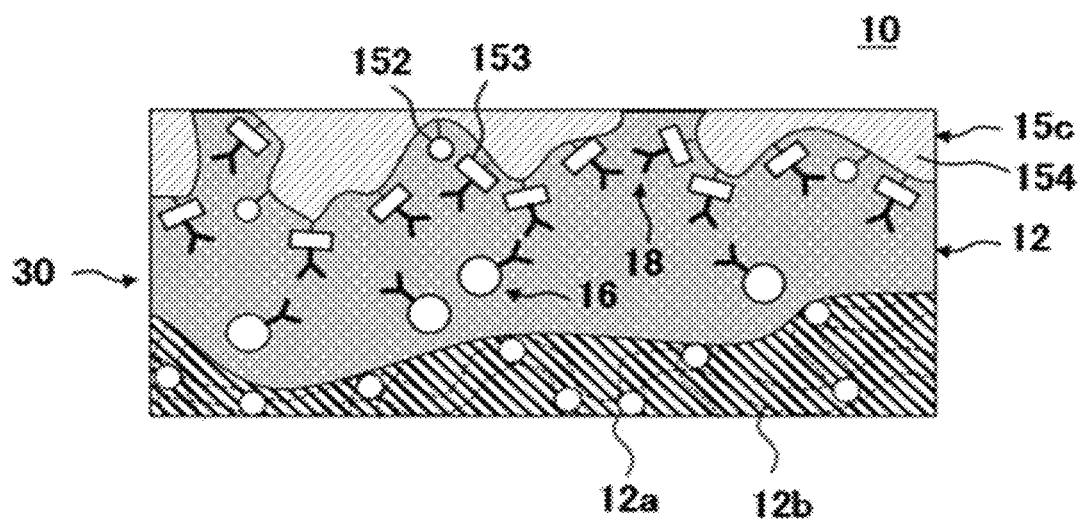
FIG. 5A is a cross-sectional view illustrating another example of a testing device, taken at a portion at which a flow path member and a resin layer face each other.
Figure 5B:
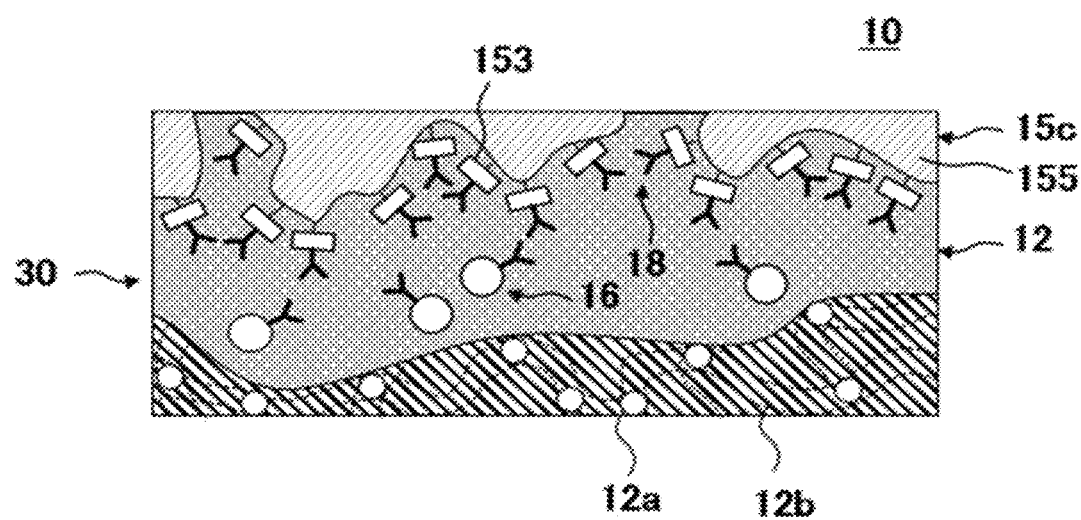
FIG. 5B is a cross-sectional view illustrating another example of a testing device, taken at a portion at which a flow path member and a resin layer face each other.

As illustrated in FIG. 4A and FIG. 4B, it is preferable that the resin layer 15b (first resin layer) be a resin containing hydrophobic groups 153. Specifically, the resin layer 15b contains a hydrophobic resin 155 or an amphiphilic resin 154 containing many hydrophobic groups 153. The hydrophobic resin 155 or the amphiphilic resin 154 is preferably a main component (accounting for 50% by mass or greater) of the resin layer 15b.

A hydrophobic group is a group of atoms having a poor intimacy with water or a poor affinity with water and is sparingly soluble in water or sparingly miscible with water.

The capture antibody 17 has a hydrophobic portion 17g. The capture antibody 17 is formed as a solid phase over a surface of the resin layer 15b facing the flow path member 12 and inside voids of the resin layer 15b, by the hydrophobic portion 17g binding with the surface and the inside of the voids by an intermolecular force. When the gap formed at the portion at which the flow path member 12 and the resin layer 15b face each other is filled with the testing liquid 30, the capture antibody 17 captures the antigen 31 that is in the state of being bound with the labeled antibody 16. As a result, the antigen 31 and the labeled antibody 16 are immobilized and develop a color. Therefore, the resin layer 15b can be used as a line for judging presence or absence of the antigen 31.

The hydrophobic resin 155 and the amphiphilic resin 154 are not particularly limited and may be appropriately selected depending on the o intended purpose. It is preferable that the both be the water-insoluble resins. When both of the hydrophobic resin 155 and the amphiphilic resin 154 are the water-insoluble resins, there is an advantage that blurring of the line can be prevented.

As illustrated in FIG. 5A and FIG. 5B, the resin layer 15c (first resin layer) contains a hydrophobic resin 155 or an amphiphilic resin 154 containing many hydrophobic groups 153. The hydrophobic resin 155 or the amphiphilic resin 154 is preferably a main component (accounting for 50% by mass or greater) of the resin layer 15c.

The capture antibody 18 is formed as a solid phase over a surface of the resin layer 15c facing the flow path member 12 and inside the voids of the resin layer 15c, by a hydrophobic portion of the capture antibody 18 binding with the surface and the inside of the voids by an intermolecular force. The capture antibody 18 is not particularly limited and may be appropriately selected depending on the intended purpose, so long as the capture antibody 18 can capture the labeled antibody 16. Examples of the capture antibody 18 include an antibody (antigen) that specifically binds with the labeled antibody 16. Hence, the labeled antibody 16 is immobilized and develops a color. Therefore, the resin layer 15c can be used as a control line for indicating that the labeled antibody 16 has arrived. The hydrophobic resin 155 and the amphiphilic resin 154 are not particularly limited and may be appropriately selected depending on the intended purpose. It is preferable that the both be the water-insoluble resins. When both of the hydrophobic resin 155 and the amphiphilic resin 154 are the water-insoluble resins, there is an advantage that blurring of the control line can be prevented.

In the present embodiment, the testing device 10 configured to test presence or absence of the antigen 31 in the testing liquid 30 is described. However, the testing device of the present disclosure is not limited to a testing device utilizing an antigen-antibody reaction. For example, the testing device may be configured to test a specific component in the testing liquid 30 by using, as a reagent, a reagent that changes hues upon a structural change.

Each member constituting the testing device 10 will be described in detail below.

<Base Material>

The base material 11 is not particularly limited and may be appropriately selected depending on the intended purpose. Examples of the base material include organic, inorganic, and metallic base materials.

The base material 11 is not particularly limited and may be appropriately selected depending on the intended purpose. However, it is preferable that at least one surface of the base material 11 be coated with a hydrophobic resin.

When the testing device 10 is used as a sensor chip, it is preferable to use a light-weight, flexible, and inexpensive synthetic resin as the base material 11.

In the present embodiment, it is optional to select a base material 11 having a high durability such as a plastic sheet. This improves the durability of the testing device 10 as a result.

A constituent material of the base material 11 is not particularly limited and may be appropriately selected depending on the intended purpose. Examples of the constituent material of the base material 11 include polyvinyl chlorides, polyethylene terephthalates, polypropylenes, polystyrenes, polyvinyl acetates, polycarbonates, polyacetals, modified polyphenyl ethers, polybutylene phthalates, and ABS resins. Among these materials, polyethylene terephthalates are preferable because polyethylene terephthalates are low-price and highly versatile.

The shape of the base material 11 is not particularly limited and may be appropriately selected depending on the intended purpose. However, a sheet shape is preferable.

The average thickness of the base material 11 is not particularly limited, may be appropriately selected depending on the intended purpose, and is preferably 0.01 mm or greater but 0.5 mm or less. When the average thickness of the base material 11 is 0.01 mm or greater, the base material 11 has an adequate strength as a base material. When the average thickness of the base material 11 is 0.5 mm or less, the base material 11 has a good flexibility and is suitable as a sensor.

The average thickness may be an average of thicknesses measured with a micrometer (MDH-25M available from Mitutoyo Corporation) at a total of 15 positions of a measuring target, namely 5 positions in the longer direction (direction of length)×3 positions in the width direction that are selected at approximately equal intervals. In the present embodiment, the average thickness may be a length of a target in a direction perpendicular to a contact plane at which the base material 11 and the flow path member 12 contact each other.

<Flow Path Member>

The flow path member 12 of the testing device 10 is not particularly limited and may be appropriately selected depending on the intended purpose so long as the flow path member is a member through which the testing liquid 30 can be flowed. Examples of the flow path member 12 include a porous material. The flow path member 12 formed of the porous material contains voids (12a and 12b), and a flow path is formed when the testing liquid 30 flows through the voids (12a and 12b).

In FIG. 3 to FIG. 5B, the void 12a is a void formed in the cross-sections, and the void 12b is a void present more backward in the cross-sections. It is preferable that cells be present in the porous material and that the cells be linked together to form a continuous cell.

The continuous cell is distinguished from independent cells that are not linked together. The continuous cell has a function of sucking in a liquid by a capillary action or letting a gas pass through the continuous cell because the continuous cell has small holes in the walls between the cells. The flow path member 12 needs no external actuating device such as a pump because the flow path member 12 is configured to deliver the testing liquid 30 by utilizing a capillary action through the voids (12a and 12b).

The porous material is not particularly limited and may be appropriately selected depending on the intended purpose. Examples of the porous material include membrane films formed of, for example, nitrocellulose, hydrophilized PTFE, hydrophilized PVDF, nylon, and vinylon.

The shape of the porous material is not particularly limited and may be appropriately selected depending on the intended purpose. However, a sheet shape is preferable.

The average thickness of the porous material is not particularly limited, may be appropriately selected depending on the intended purpose, and is preferably 0.01 mm or greater but 0.3 mm or less. When the average thickness of the porous material is 0.01 mm or greater, there is an advantage that the flow path member has a good strength. When the average thickness of the porous material is 0.3 mm or less, there is an advantage that the amount of the testing liquid needed can be optimized.

<Resin Layer>

The function of the resin layer 15 will be described based on comparison with an existing testing device illustrated in FIG. 6 and FIG. 7.

Figure 6:
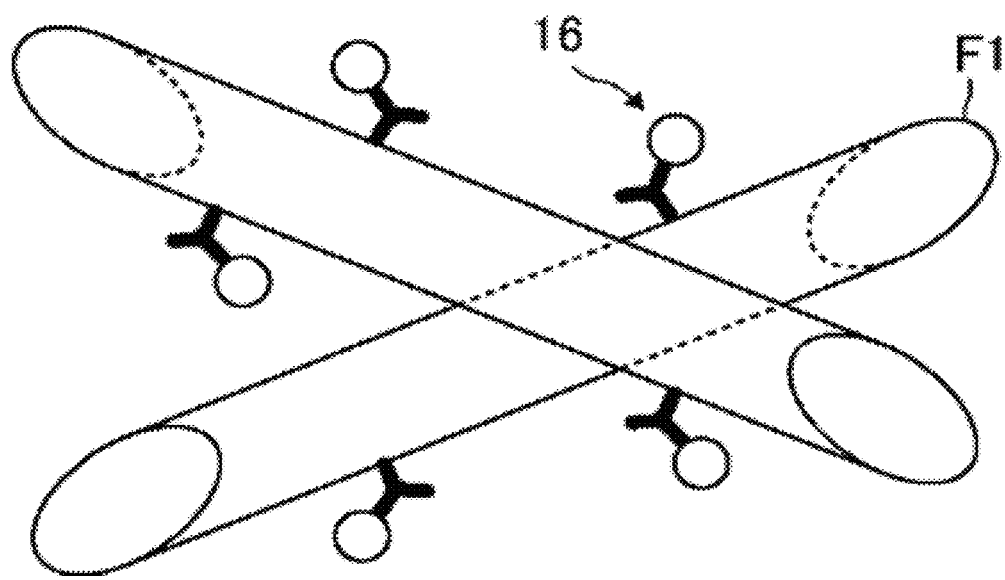
FIG. 6 is a conceptual diagram of a conjugate pad of an existing testing device.

FIG. 6 is a conceptual diagram of a conjugate pad of an existing testing device. FIG. 7 is a conceptual diagram of a membrane of an existing testing device.

In the existing testing device, when the conjugate pad has an extremely high hydrophilicity, a testing liquid tends to stay within the conjugate pad and does not easily flow into the membrane. Conversely, when the conjugate pad has an extremely high hydrophobicity, the testing liquid smoothly flows into the membrane, but a long time is needed for testing or the testing liquid is needed in a large amount because the conjugate pad has a poor absorbency for absorbing the testing liquid from the sample pad. Hence, fiber F1 usable for the conjugate pad is limited. Furthermore, in the existing testing device, the labeled antibody 16 is formed as a solid phase on the fiber F1 constituting the conjugate pad (see FIG. 6). The labeled antibody 16 can be released from the conjugate pad only when the labeled antibody 16 has a weak force of binding with the fiber F1. That is, as a matter of design, the existing testing device is limited in the fiber F1 and the labeled antibody 16 that can be used.

Figure 7:
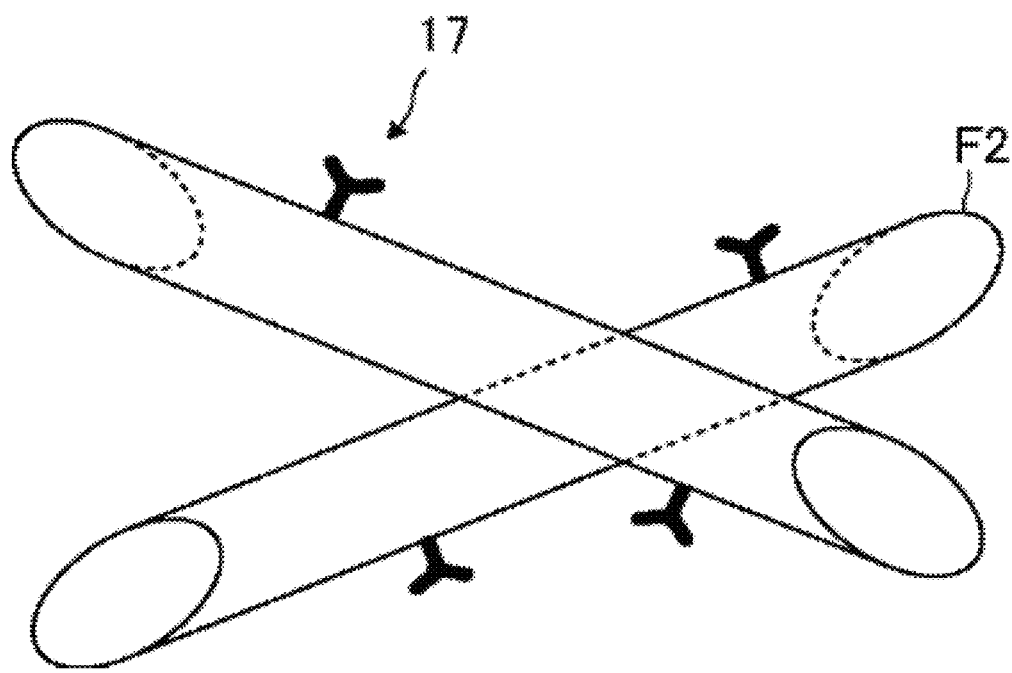
FIG. 7 is a conceptual diagram of a membrane of an existing testing device.

Likewise, in the existing testing device, the capture antibody 17 is formed as a solid phase on fiber F2 constituting the membrane (see FIG. 7). Hence, the capture antibody 17 can be immobilized to the membrane only when the capture antibody 17 has a strong force of binding with the fiber F2. That is, as a matter of design, the existing testing device is limited in the fiber F2 and the capture antibody 17 that can be used.

In the testing device 10, the reagents such as the labeled antibody 16, the capture antibody 17, and the capture antibody 18 are formed as solid phases over the resin layers 15 (15a, 15b, and 15c). Hence, release of the labeled antibody 16 or immobilization of the capture antibody 17 can be controlled based on the intensity of interaction between the resin layer 15 and the capture antibody 17 and affinity between the resin layer 15 and the testing liquid 30.

As the method for adjusting the intensity of interaction between the resin layer 15 and the capture antibody 17 and affinity between the resin layer 15 and the testing liquid 30, for example, there is a method of changing the kinds of the resins to constitute the resin layer 15 or the composition ratio of the resins in a manner to match the corresponding capture antibody 17. For example, the higher the hydrophobic percentage in the resin constituting the resin layer 15, the easier it is to immobilize the capture antibody 17 containing a hydrophobic group to the resin layer 15 based on hydrophobic interaction.

The hydrophobic interaction refers to a cause (driving force) of a change occurring in water that hydrophobic molecules or hydrophobic groups immiscible with water aggregate with each other. To be more specific, when hydrophobic molecules or molecules having hydrophobic groups are put in water, in many cases, these molecules not only simply do not dissolve but come into a state of the hydrophobic molecules and the hydrophobic groups contacting each other to reduce the area of contact with water molecules as much as possible. The hydrophobic interaction refers to a consequent phenomenon that the hydrophobic molecules attract each other and seem to have a binding force acting between the molecules.

When the hydrophilic percentage is high in the resin constituting the resin layer 15, the resin layer 15 has a strong interaction with a hydrophilic reagent. However, it is estimated that when the bonding portion between the resin layer and the labeled antibody contacts the hydrophilic testing liquid 30, the reagent comes to have affinity with the testing liquid 30 and is easily released into the testing liquid 30.

The resin constituting the resin layer 15 is preferably a water-insoluble resin. When the resin constituting the resin layer 15 is the water-insoluble resin, the resin can be kept from being dissolved in the testing liquid 30 and hence clogging the flow path or smudging the control line or the test line.

The amphiphilic resin constituting the resin layer 15a is not particularly limited and may be appropriately selected depending on the intended purpose. Examples of the amphiphilic resin include polyvinyl alcohol resins, polyvinylacetal resins, polyacrylic acids, polyacrylic acid-acrylonitrile copolymers, vinyl acetate-acrylic acid ester copolymers, acrylic acid-acrylic acid ester copolymers, styrene-acrylic acid copolymers, styrene-methacrylic acid copolymers, styrene-methacrylic acid-acrylic acid ester copolymers, styrene-a-methylstyrene-acrylic acid copolymers, styrene-a-methylstyrene-acrylic acid-acrylic acid ester copolymers, styrene-maleic acid copolymers, styrene-maleic anhydride copolymers, vinyl naphthalene-acrylic acid copolymers, vinyl naphthalene-maleic acid copolymers, vinyl acetate-maleic acid ester copolymers, vinyl acetate-crotonic acid copolymers, vinyl acetate-acrylic acid copolymers, and salts of these amphiphilic resins One of these amphiphilic resins may be used alone or two or more of these amphiphilic resins may be used in combination.

Among these amphiphilic resins, copolymers of hydrophobic functional group-containing monomers and hydrophilic functional group-containing monomers and polymers formed of monomers containing both of hydrophobic functional groups and hydrophilic functional groups are preferable.

As the form of the copolymers, any of random copolymers, block copolymers, alternating copolymers, and graft copolymers may be used.

Examples of the hydrophobic resin constituting the resin layer 15b and the resin layer 15c include: polystyrene-based resins such as polystyrenes and acrylonitrile-butadiene-styrene copolymers; polyolefin-based resins or cyclic polyolefin-based resins such as polypropylene resins, polyethylene resins, and ethylene-propylene copolymers; polycarbonate resins, polyethylene terephthalate resins, and methacrylic-based resins such as polymethyl methacrylate resins; vinyl chloride resins, polybutylene terephthalate resins, polyarylate resins, polysulfone resins, polyether sulfone resins, polyether ether ketone resins, and polyether imide resins; fluororesins such as polytetrafluoroethylene; acrylic-based resins such as polymethylpentene resins and polyacrylonitrile; and cellulose-based resins such as propionate resins. One of these hydrophobic resins may be used alone or two or more of these hydrophobic resins may be used in combination.

Examples of compounds that may constitute the resin layer 15b and the resin layer 15c other than the hydrophobic resins include: natural waxes such as beeswax, carnauba wax, cetaceum, Japan wax, candelilla wax, rice bran wax, and montan wax; synthetic waxes such as paraffin wax, microcrystalline wax, oxidized wax, ozokerite, ceresin, ester wax, polyethylene wax, and polyethylene oxide wax; higher fatty acids such as margaric acid, lauric acid, myristic acid, palmitic acid, stearic acid, furoic acid, and behenic acid; higher alcohols such as stearic alcohol and behenyl alcohol; esters such as fatty acid ester of sorbitan; and amides such as stearin amide and oleic amide. One of these compounds may be used alone or two or more of these compounds may be used in combination.

Among the compounds that may constitute the resin layer 15b and the resin layer 15c, polystyrene resins, polyolefin resins, carnauba wax, and polyethylene wax are preferable because these compounds have a strong hydrophobic interaction.

The resin layers (15a, 15b, and 15c) may be formed of the same resin. In this case, it is preferable that the resin constituting the resin layer 15a be higher in hydrophilicity than the resins constituting the resin layers (15b and 15c). Note that the same resin can be said to have a higher hydrophilicity when the percentage of hydrophilic groups is higher, without the need for measuring hydrophilicity.

The labeled antibody 16 to be formed as a solid phase over the resin layer 15a is not particularly limited and may be appropriately selected depending on the intended purpose, so long as the labeled antibody 16 has a hydrophilic portion and is reactive with the antigen 31. Examples of the labeled antibody 16 include antibodies labeled with gold colloid particles, and particles for labeling other antibodies.

The particles for labeling other antibodies are not particularly limited to gold colloid and may be appropriately selected depending on the intended purpose. Examples of such particles include metal colloids other than gold colloid, enzymatic labeling particles containing an enzyme, coloring particles containing a pigment, fluorescent particles containing a fluorescent substance, and magnetic body encapsulating particles containing a magnetic body. One of these kinds of particles may be used alone or two or more of these kinds of particles may be used in combination.

The antibody may be in any form of monoclonal antibody, polyclonal antibody, chimeric antibody, Fab antibody, and (Fab)$_2$ antibody.

The capture antibody 17 to be formed as a solid phase over the resin layer 15b is not particularly limited and may be appropriately selected depending on the intended purpose, so long as the capture antibody 17 has a hydrophobic portion and is reactive with the antigen 31. Examples of the capture antibody 17 include IgG antibodies.

The antibody may be in any form of monoclonal antibody, polyclonal antibody, chimeric antibody, Fab antibody, and (Fab)$_2$ antibody.

The capture antibody 18 to be formed as a solid phase over the resin layer 15c is not particularly limited and may be appropriately selected depending on the intended purpose, so long as the capture antibody 18 has a hydrophobic group and is reactive with the labeled antibody 16. Examples of the capture antibody 18 include antibodies such as IgG against the labeled antibody 16 and antibodies raised as examples above. The capture antibody 18 may also be the very antigen that is reactive with the labeled antibody 16.

The method for forming the reagents such as the labeled antibody 16 and the capture antibodies (17 and 18) as solid phases over the resin layers 15 is not particularly limited and may be appropriately selected depending on the intended purpose. Examples of the method include a method of coating and impregnating the resin layer 15 with a solution containing a reagent and then drying up the solution by fast drying, and a method of coating and impregnating the resin layer 15 with a solution containing a reagent, leaving the resin layer standing still (for incubation) in a high humidity environment so as not for the coating liquid to dry, cleaning away any other components than the antibody such as an inorganic salt with, for example, distilled water, and then drying the antibody.

Particularly, examples of the method for forming the reagents such as the capture antibodies (17 and 18) as solid phases inside the voids of the resin layers (15b and 15c) include a pressure impregnation method, a vacuum impregnation method, and a vacuum pressure impregnation method. The resin layers are formed of a hydrophobic material and the internal walls of the voids exhibit hydrophobicity. Therefore, simply coating the antibody coating liquid cannot allow smooth permeation of the antibody coating liquid into the voids. There is also a case where a gas remaining inside the voids may disturb permeation of the coating liquid. Hence, pressure application after the antibody coating liquid is coated over the resin layer or after the resin layer is impregnated with the antibody coating liquid allows the solution to be pushed into the voids. This makes it possible for the voids to be full of the antibody coating liquid. After the resin layers are impregnated with the solution containing the reagent by the method described above, the dry-up method and the incubation may be performed for the reagent to be formed as a solid phase.

It is preferable that the resin layer 15 be secured over the flow path member 12.

The method for securing the resin layer 15 over the flow path member 12 is not particularly limited and may be appropriately selected depending on the intended purpose, so long as the method secures the resin layer 15 in a manner that the reagent and the testing liquid 30 can contact each other during testing. Examples of the method include a method of thermally transferring the resin to constitute the resin layer onto the flow path member 12 with, for example, a thermal transfer printer, a method of transferring the resin to constitute the resin layer with a pressure applied with, for example, a dot impact printer, and a method of pasting the resin to constitute the resin layer over the flow path member 12 with, for example, a tape, an adhesive, or a tackifier.

<Absorbing Member>

The absorbing member 14 is not particularly limited so long as the absorbing member 14 is a member configured to absorb water, and may be appropriately selected from known materials.

Examples of the absorbing member 14 include fiber such as paper and cloth, polymer compounds containing a carboxyl group or a salt of a carboxyl group, partially cross-linked bodies of polymer compounds containing a carboxyl group or a salt of a carboxyl group, and partially cross-linked bodies of polysaccharides.

<Other Members>

The other members are not particularly limited and may be appropriately selected depending on the intended purpose. Examples of the other members include a protective member, a labeled antibody support pad, and a sample dropping pad.

The protective member is a member intended for preventing contamination of a hand when the hand touches the flow path member.

The protective member is not particularly limited and may be appropriately selected depending on the intended purpose. Examples of the protective member include a housing configured to cover the testing device on the whole and a film provided over the flow path member.

When providing the protective member, it is preferable that an opening be provided in the protective member at a position to be above the dropping portion of the flow path member 12. It is preferable that an opening be provided in the protective member in order to release pressure in the flow path.

As described above, the resin layers 15 can be provided over the flow path member 12 by various methods. As an example, a case of using a thermal transfer method will be described. A transfer medium for a testing device used in the thermal transfer method and a method for producing a testing device will be described below.

(Transfer Medium for Testing Device)

A transfer medium for a testing device of the present disclosure includes a support and a solid-phase reagent layer provided over the support. The solid-phase reagent layer is a porous body formed of a hydrophobic material. A reagent reactive with a sample is formed as a solid phase over a surface of the solid-phase reagent layer opposite to a surface of the solid-phase reagent layer facing the support and inside voids of the solid-phase reagent layer.

It is preferable that a release layer be provided between the support and the solid-phase reagent layer.

It is preferable that the solid-phase reagent layer be a release and solid-phase reagent layer that serves also as a release layer. In this case, the release and solid-phase reagent layer is a porous body formed of a hydrophobic material, and a reagent reactive with a sample is provided over a surface of the release and solid-phase reagent layer facing the flow path member and inside voids of the release and solid-phase reagent layer.

It is preferable that the material constituting the solid-phase reagent layer have a contact angle of 75 degrees C. or greater with respect to distilled water at 25 degrees C.

It is preferable that the voidage of the solid-phase reagent layer before formation of a reagent as a solid phase be 10% or higher but 45% or lower.

Figure 8A:
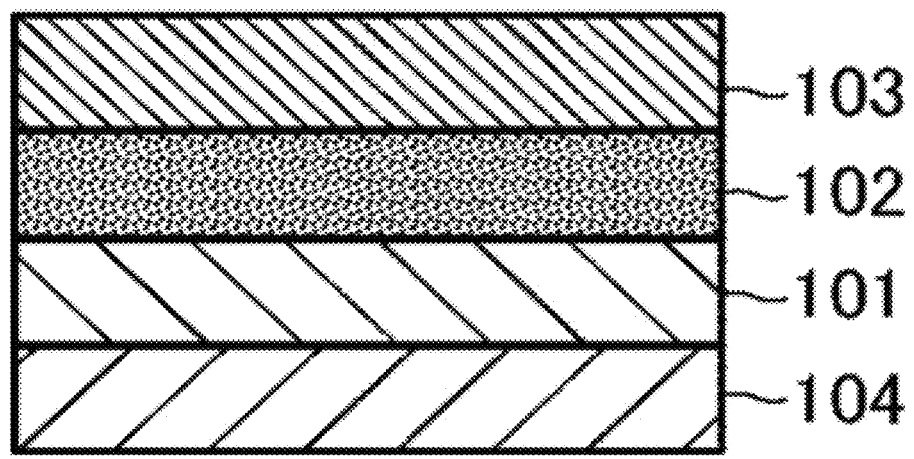
FIG. 8A is a schematic cross-sectional view illustrating an example of a transfer medium for a testing device of the present disclosure.
Figure 8B:
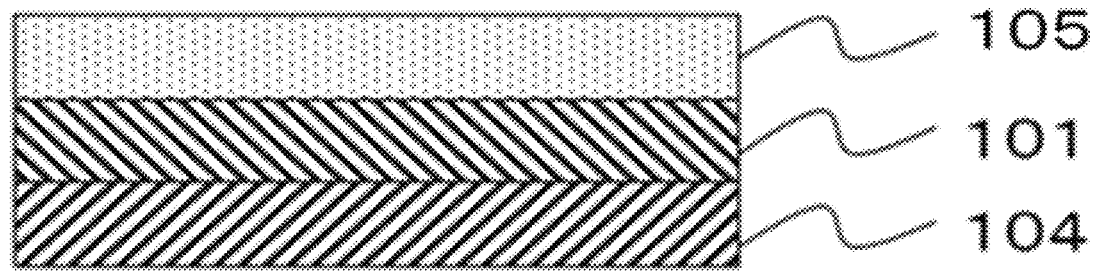
FIG. 8B is a schematic cross-sectional view illustrating another example of a transfer medium for a testing device of the present disclosure.

Here, a transfer medium for a testing device used for providing a resin layer over a flow path member will be described with reference to the drawings. FIG. 8A is a schematic cross-sectional view illustrating an example of a transfer medium for a testing device of the present disclosure. FIG. 8B is a schematic cross-sectional view illustrating another example of a transfer medium for a testing device of the present disclosure.

When employing a thermal transfer method, it is possible to use a transfer medium 100 for a testing device to which a capture antibody is previously attached uniformly. This can suppress variation in the concentration of the capture antibody (17 or 18) along a test line or a control line. When coating and locating a capture antibody by an existing method, there is a need for diluting the capture antibody with a solvent until the capture antibody has a viscosity of a coatable level (e.g., a viscosity dischargeable by an inkjet printer). On the other hand, when locating a capture antibody by thermal transfer, use of a transfer medium lo for a testing device to which a capture antibody is previously attached at a high concentration enables location of the capture antibody over a flow path at a high concentration.

As illustrated in FIG. 8A, the transfer medium 100 for a testing device includes a support 101, a release layer 102 provided over the support 101, and a solid-phase reagent layer 103 provided over the release layer 102. A reagent is formed as a solid phase over a surface of the solid-phase reagent layer 103. The transfer medium 100 for a testing device further includes other layers such as a back layer 104 as needed.

As represented by a transfer medium 110 for a testing device of FIG. 8B, a release layer 102 and a solid-phase reagent layer 103 may be provided in the form of a double-functioning release and solid-phase reagent layer 105.

<Support>

The support 101 may be of any shape, any structure, any size, any material, etc. that are not particularly limited and may be appropriately selected depending on the intended purpose.

The structure of the support may be a single-layer structure or a laminated structure.

The size of the support may be appropriately selected depending on, for example, the size of the testing device.

The material of the support 101 is not particularly limited and may be appropriately selected depending on the intended purpose. Examples of the material of the support 101 include polyesters such as polyethylene terephthalate (PET) and polyethylene naphthalate (PEN), polycarbonates, polyimide resins (PI), polyamides, polyethylenes, polypropylenes, polyvinyl chlorides, polyvinylidene chlorides, polystyrenes, styrene-acrylonitrile copolymers, and cellulose acetates. One of these materials may be used alone or two or more of these materials may be used in combination. Among these materials, polyethylene terephthalate (PET) and polyethylene naphthalate (PEN) are particularly preferable.

It is preferable to apply a surface activation treatment to the surface of the support 101 in order to improve close adhesiveness with the layer to be provided over the support 101. Examples of the surface activation treatment include glow discharge treatment and corona discharge treatment.

The support 101 may be kept even after the solid-phase reagent layer 103 is transferred onto a flow path member 12, or the support 101, etc. may be peeled and removed by means of the release layer 102 after the solid-phase reagent layer 103 is transferred. When the release and solid-phase reagent layer 105 is used, the release and solid-phase reagent layer 105 may be completely transferred onto the flow path member 12, or a portion of the release and solid-phase reagent layer 105 including the surface over which the antibody is formed as a solid phase may be transferred but the release and solid-phase reagent layer 105 may be partially left over the support 101 side.

The support 101 is not particularly limited and may be an appropriately synthesized product or a commercially available product.

The average thickness of the support 101 is not particularly limited, may be appropriately selected depending on the intended purpose, and is preferably 3 micrometers or greater but 50 micrometers or less.

<Release Layer>

The release layer 102 has a function of improving releasability between the support 101 and the solid-phase reagent layer 103 during transfer. The release layer 102 has a function of thermally melting and becoming a low-viscosity liquid when heated with a heating/pressurizing unit such as a thermal head, and making it easier for the solid-phase reagent layer 103 to be separated at about the interface between the heated portion and the non-heated portion.

The release layer 102 contains a wax and a binder resin and further contains other components as needed.

The wax is not particularly limited and may be appropriately selected depending on the intended purpose. Examples of the wax include: natural waxes such as beeswax, carnauba wax, cetaceum, Japan wax, candelilla wax, rice bran wax, and montan wax; synthetic waxes such as paraffin wax, microcrystalline wax, oxidized wax, ozokerite, ceresin, ester wax, polyethylene wax, and polyethylene oxide wax; higher fatty acids such as margaric acid, lauric acid, myristic acid, palmitic acid, stearic acid, furoic acid, and behenic acid; higher alcohols such as stearic alcohol and behenyl alcohol; esters such as fatty acid ester of sorbitan; and amides such as stearin amide and oleic amide. One of these waxes may be used alone or two or more of these waxes may be used in combination. Among these waxes, carnauba wax and polyethylene wax are preferable because these waxes are excellent in releasability.

The binder resin is not particularly limited and may be appropriately selected depending on the intended purpose. Examples of the binder resin include ethylene-vinyl acetate copolymers, partially saponified ethylene-vinyl acetate copolymers, ethylene-vinyl alcohol copolymers, ethylene-sodium methacrylate copolymers, polyamides, polyesters, polyurethanes, polyvinyl alcohols, methylcellulose, carboxymethylcellulose, starch, polyacrylic acid, isobutylene-maleic acid copolymers, styrene-maleic acid copolymers, polyacrylamides, polyvinylacetals, polyvinyl chlorides, polyvinylidene chlorides, isoprene rubbers, styrene-butadiene copolymers, ethylene-propylene copolymers, butyl rubbers, and acrylonitrile-butadiene copolymers. One of these binder resins may be used alone or two or more of these binder resins may be used in combination.

The method for forming the release layer 102 is not particularly limited and may be appropriately selected depending on the intended purpose. Examples of the method include a hot melt coating method, and a method of coating a coating liquid obtained by dispersing the wax and the binder resin in a solvent.

The average thickness of the release layer 102 is not particularly limited, may be appropriately selected depending on the intended purpose, and is preferably 0.5 micrometers or greater but 50 micrometers or less.

The amount of the release layer 102 to be attached is not particularly limited, may be appropriately selected depending on the intended purpose, and is preferably 0.5 g/m$^2$ or greater but 50 g/m$^2$ or less.

<Solid-phase Reagent Layer>

The solid-phase reagent layer 103 needs to contain a resin that constitutes a resin layer 15 of the testing device 10. The material of the solid-phase reagent layer 103 is not particularly limited and may be appropriately selected depending on the intended purpose.

The method for forming the solid-phase reagent layer 103 is not particularly limited and may be appropriately selected depending on the intended purpose. Examples of the method include a hot melt coating method and a method of coating a solid-phase reagent layer coating liquid obtained by dispersing the resin that constitutes the resin layer 15 in a solvent over the support 101 or the release layer 102 by a common coating method such as a gravure coater, a wire bar coater, and a roll coater, and drying the coated liquid.

The average thickness of the solid-phase reagent layer 103 is not particularly limited, may be appropriately selected depending on the intended purpose, and is preferably 200 nm or greater but 50 micrometers or less. When the average thickness of the solid-phase reagent layer 103 is 200 nm or greater, the resin layer 15 has an improved durability and can be prevented from being damaged by, for example, friction and impact. When the average thickness of the solid-phase reagent layer 103 is 50 micrometers or less, heat from a thermal head can be uniformly conducted to the solid-phase reagent layer 103, resulting in a good definition.

The amount of a reagent coating liquid attached over the solid-phase reagent layer 103 is not particularly limited, may be appropriately selected depending on the intended purpose, and is preferably 0.2 g/m$^2$ or greater but 50 g/m$^2$ or less. When the amount of the reagent coating liquid attached is 0.2 g/m$^2$ or greater, the coating amount is appropriate and no deficiency is created in the resin layer. When the amount of the reagent coating liquid attached is 50 g/m$^2$ or less, a drying time is appropriate and no unevenness is formed in the resin layer.

<Release and Solid-phase Reagent Layer>

The release and solid-phase reagent layer 105 has functions of both of the release layer 102 and the solid-phase reagent layer 103. The release and solid-phase reagent layer 105 can improve releasability between the support 101 and the solid-phase reagent layer 103 during transfer. Further, because the resin that constitutes the resin layer 15 of the testing device 10 is contained in the release and solid-phase reagent layer 105, a reagent such as the capture antibody 17 or the capture antibody 18 can be formed as a solid phase over the release and solid-phase reagent layer 105.

When the release and solid-phase reagent layer 105 is heated with a heating/pressurizing unit such as a thermal head, a surface of the release and solid-phase reagent layer 105 contacting the support 101 thermally melts and becomes a low-viscosity liquid (heated portion), whereas a surface of the release and solid-phase reagent layer 105 provided with the reagent as a solid phase becomes a solid state or a state close to the solid state (non-heated portion). Therefore, the release and solid-phase reagent layer 105 has a function of facilitating separation at about the interface between the heated portion and the non-heated portion.

The release and solid-phase reagent layer 105 contains a wax and a binder resin, and further contains other components as needed.

The wax is not particularly limited and may be appropriately selected depending on the intended purpose. Examples of the wax include the same waxes as raised as examples for the release layer 102. One of these waxes may be used alone or two or more of these waxes may be used in combination. Among these waxes, carnauba wax and polyethylene wax are preferable because these waxes are excellent in releasability and ability (hydrophobicity) to immobilize a capture antibody.

The binder resin is not particularly limited and may be appropriately selected depending on the intended purpose. Examples of the binder resin include the same binder resins as raised as examples for the release layer 102. One of these binder resins may be used alone or two or more of these binder resins may be used in combination.

The method for forming the release and solid-phase reagent layer 105 is not particularly limited and may be appropriately selected depending on the intended purpose. Examples of the method include a hot melt coating method, and a method of coating a coating liquid obtained by dispersing the wax and the binder resin in a solvent.

The average thickness of the release and solid-phase reagent layer 105 is not particularly limited, may be appropriately selected depending on the intended purpose, and is preferably 0.5 micrometers or greater but 50 micrometers or less. When the average thickness of the release and solid-phase reagent layer 105 is 0.5 micrometers or greater, the release and solid-phase reagent layer 105 (resin layer 15) has an improved durability and the resin layer can be prevented from being damaged by, for example, friction and impact. When the average thickness of the release and solid-phase reagent layer 105 is 50 micrometers or less, heat from a thermal head can be uniformly conducted to the release and solid-phase reagent layer 105, resulting in a good definition.

The amount of the release and solid-phase reagent layer 105 attached is not particularly limited, may be appropriately selected depending on the intended purpose, and is preferably 0.5 $g/m^2$ or greater but 50 $g/m^2$ or less. When the amount of the release and solid-phase reagent layer 105 attached is 0.5 $g/m^2$ or greater, the coating amount is appropriate and no deficiency is created in the release and solid-phase reagent layer 105 (resin layer 15). When the amount of the release and solid-phase reagent layer 105 attached is 50 $g/m^2$ or less, a drying time is appropriate and no unevenness is formed in the release and solid-phase reagent layer 105.

—Formation of Reagent as Solid-phase—

After the coating liquid is dried and the solid-phase reagent layer 103 or the release and solid-phase reagent layer 105 is formed, a solution containing the labeled antibody 16 or the capture antibody (17 or 18) is coated over the surface of the solid-phase reagent layer 103 or the release and solid-phase reagent layer 105, to form a coating film. For the labeled antibody 16, the method of drying up the coated solution by fast drying is preferable. For the capture antibody (17 or 18), impregnation of the voids with the solution may be performed by, for example, a pressure impregnation method, a vacuum impregnation method, or a vacuum pressure impregnation method, and then a dry-up method or incubation may be performed for the reagent to be formed as a solid phase.

—Formation of Labeled Antibody as Solid Phase—

The method for forming the labeled antibody as a solid phase is not particularly limited and may be appropriately selected depending on the intended purpose. Examples of the method include a method of coating a coating liquid of the labeled antibody over the surface of the solid-phase reagent layer 103 or the release and solid-phase reagent layer 105 to form a water film and drying up the water film by, for example, natural drying, drying under reduced pressure, or freeze drying to form the water film as a solid phase.

It is preferable that the water film be coated to have a uniform thickness.

An amount of the labeled antibody coated is not particularly limited and may be appropriately selected depending on the intended purpose. When using a gold colloid labeled antibody as the labeled antibody, it is preferable to coat a gold colloid labeled antibody having an OD (optical density) of from 1.0 through 20 in a coating amount of 5 microliters or greater but 600 microliters or less per unit area ($cm^2$) of the resin layer. When the coating amount of the labeled antibody is 5 microliters or greater, the amount of the gold colloid labeled antibody is appropriate and a color developing density on a line is good. When the coating amount of the labeled antibody is 600 microliters or less, the amount of the gold colloid labeled antibody is appropriate and color development on a line is good.

The method for drying the coating liquid is not particularly limited and may be appropriately selected depending on the intended purpose. Examples of the drying method include through-flow drying, vacuum drying, natural drying, and freeze drying. Among these drying methods, natural drying under a low humidity or drying under reduced pressure is preferable.

A humidity during drying is not particularly limited, may be appropriately selected depending on the intended purpose, and is preferably 30% or lower on a relative humidity basis. When the humidity during drying is 30% or lower on the relative humidity basis, there is an advantage that drying is appropriate and the antibody can be formed as a sufficiently solid phase.

A drying temperature for drying the coating liquid is not particularly limited, may be appropriately selected depending on the intended purpose, and is preferably −40 degrees C. or higher but 50 degrees C. or lower. When the drying temperature is −40 degrees C. or higher, drying of the coating liquid can be performed appropriately and productivity is improved. When the drying temperature is 50 degrees C. or lower, there is an advantage that the reagent can be prevented from being denatured by heat. Note, however, that there may be a case where it is preferable to set the upper limit temperature to be lower, depending on the kind of the labeled antibody. A drying time for drying the coating liquid is not particularly limited, may be appropriately selected depending on the intended purpose, and is preferably 24 hours or shorter. When the drying time is 24 hours or shorter, there is an advantage that productivity is improved and discoloring can be prevented.

—Formation of Capture Antibody as Solid Phase—

The method for forming the capture antibody as a solid phase is not particularly limited and may be appropriately selected depending on the intended purpose. Examples of the method include a method (dry-up method) of coating a coating liquid of the capture antibody over the surface of the solid-phase reagent layer 103 or the release and solid-phase reagent layer 105 to form a water film, impregnating the voids with the solution by, for example, a pressure impregnation method, a vacuum impregnation method, or a vacuum pressure impregnation method, and then drying up the water film or the solution by, for example, natural drying, drying under reduced pressure, or freeze drying to form the water film or the solution as a solid phase, and a method (adsorption drying method) of leaving the coating liquid standing still under a high humidity environment so as not for the coating liquid to dry, cleaning the surface of the solid-phase reagent layer 103 or the release and solid-phase reagent layer 105 with, for example, distilled water as needed, and drying the coating liquid to a solid phase. In either case, it is preferable that the coating film be coated to have a uniform thickness.

The conditions for impregnating the voids with the solution by, for example, a pressure impregnation method, a vacuum impregnation method, and a vacuum pressure impregnation method are as described above, but are not limited to as described above.

The drying method used when forming the capture antibody as a solid phase by the dry-up method is not particularly limited and may be appropriately selected depending on the intended purpose. Examples of the drying method include through-flow drying, vacuum drying, natural drying, and freeze drying. Among these drying methods, natural drying under a low humidity or drying under reduced pressure is preferable.

A humidity during drying of the coating liquid is not particularly limited, may be appropriately selected depending on the intended purpose, and is preferably 30% or lower on a relative humidity basis. When the humidity during drying is 30% or lower on the relative humidity basis, there is an advantage that drying is appropriate and the antibody can be formed as a sufficiently solid phase.

A drying temperature for drying the coating liquid is not particularly limited, may be appropriately selected depending on the intended purpose, and is preferably −40 degrees C. or higher but 50 degrees C. or lower. When the drying temperature is −40 degrees C. or higher, drying of the coating liquid can be performed appropriately and productivity is improved. When the drying temperature is 50 degrees C. or lower, there is an advantage that the reagent can be prevented from being denatured by heat. Note, however, that there may be a case where it is preferable to set the upper limit temperature to be lower, depending on the kind of the capture antibody.

A drying time for drying the coating liquid is not particularly limited, may be appropriately selected depending on the intended purpose, and is preferably 24 hours or shorter. When the drying time is 24 hours or shorter, there is an advantage that productivity is improved and discoloring can be prevented.

Preferable standing-still conditions when forming the capture antibody as a solid phase by the adsorption drying method include a temperature of 0 degrees C. or higher but 40 degrees C. or lower. When the temperature among the standing-still conditions is 0 degrees C. or higher, it is possible to perform formation of the capture antibody as a solid phase appropriately. When the temperature is 40 degrees C. or lower, there is an advantage that the capture antibody is not denatured.

A relative humidity among the standing-still conditions is preferably 30% or higher. When the relative humidity among the standing-still conditions is 30% or higher, water volatilization during standing still is low, and this advantageously prevents any undesirable component other than the antibody from being included in the solid phase in a large amount.

The cleaning method after standing still is not particularly limited and may be appropriately selected depending on the intended purpose. Examples of the cleaning method include a method of pouring, for example, distilled water in an amount of 20 microliters or greater but 100 microliters or less per unit area (cm$^2$) onto the surface over which a solid phase is to be formed, using, for example, a shaker, and cleaning the surface at room temperature by gentle shaking.

The drying method is not particularly limited and may be appropriately selected depending on the intended purpose. Examples of the drying method include through-flow drying, vacuum drying, natural drying, and freeze drying. Among these drying methods, natural drying under a low humidity or drying under reduced pressure is preferable.

The humidity during drying is preferably 30% or lower on a relative humidity basis. When the relative humidity is 30% or lower, drying is appropriate and the antibody can be formed as a sufficiently solid phase.

The drying temperature is not particularly limited, may be appropriately selected depending on the intended purpose, and is preferably room temperature (20 degrees C.) or higher but 50 degrees C. or lower. Note, however, that there may be a case where it is preferable to set the upper limit temperature to be lower, depending on the kind of the capture antibody. When the drying temperature is 20 degrees C. or higher, a drying time is appropriate and productivity is improved. When the drying temperature is 50 degrees C. or lower, the reagent can be prevented from being denatured by heat.

The drying time is not particularly limited, may be appropriately selected depending on the intended purpose, and is preferably 24 hours or shorter. When the drying time is 24 hours or shorter, productivity is improved and discoloring of the resin can be prevented.

<Back Layer>

It is preferable that the transfer medium 100 for a testing device include a back layer 104 over a surface of the support 101 opposite to the surface of the support 101 provided with the release layer 102. During transfer, heat from, for example, a thermal head is directly applied to the opposite surface in a manner to match the shape of the resin layer. Therefore, it is preferable that the back layer 104 have resistance to a high heat and resistance to friction with, for example, the thermal head.

The back layer 104 contains a binder resin and further contains other components as needed.

The binder resin is not particularly limited and may be appropriately selected depending on the intended purpose. Examples of the binder resin include silicone-modified urethane resins, silicone-modified acrylic resins, silicone resins, silicone rubbers, fluororesins, polyimide resins, epoxy resins, phenol resins, melamine resins, and nitrocellulose. One of these binder resins may be used alone or two or more of these binder resins may be used in combination.

The other components are not particularly limited and may be appropriately selected depending on the intended purpose. Examples of the other components include inorganic particles of, for example, talc, silica, or organopolysiloxane, and a lubricant.

The method for forming the back layer 104 is not particularly limited and may be appropriately selected depending on the intended purpose. Examples of the method include a gravure coater, a wire bar coater, and a roll coater.

The average thickness of the back layer 104 is not particularly limited, may be appropriately selected depending on the intended purpose, and is preferably 0.01 micrometers or greater but 1.0 micrometer or less.

<Undercoat Layer>

An undercoat layer may be provided between the support 101 and the release layer 102 and between the release layer 102 and the solid-phase reagent layer 103, or between the support 101 and the release and solid-phase reagent layer 105.

The undercoat layer contains a resin, and further contains other components as needed.

The resin is not particularly limited and may be appropriately selected depending on the intended purpose. Examples of the resin include the resins used in the solid-phase reagent layer 103, the release layer 102, and the release and solid-phase reagent layer 105.

<Protective Film>

It is preferable to provide a protective film over the solid-phase reagent layer 103 or the release and solid-phase reagent layer 105 for protection from contamination and damage during storage.

The material of the protective film is not particularly limited and may be appropriately selected depending on the intended purpose so long as the material can be easily peeled from the solid-phase reagent layer 103 or the release and solid-phase reagent layer 105. Examples of the material of the protective film include silicone paper, polyolefin sheet such as of polypropylene, and polytetrafluoroethylene sheet.

The average thickness of the protective film is not particularly limited, may be appropriately selected depending on the intended purpose, and is preferably 5 micrometers or greater but 100 micrometers or less and more preferably 10 micrometers or greater but 30 micrometers or less.

(Method for Producing Testing Device)

A method for producing a testing device of the present disclosure includes a step of bringing the solid-phase reagent layer (or the release and solid-phase reagent layer) of the transfer medium for a testing device of the present disclosure into contact with a porous flow path member to transfer the solid-phase reagent layer (or the release and solid-phase reagent layer) onto the flow path member (this step may hereinafter be referred to as "solid-phase reagent layer transfer step"), and further includes other steps as needed.

<Solid-phase Reagent Layer Transfer Step>

Examples of the method for thermally transferring the solid-phase reagent layer (or the release and solid-phase reagent layer) onto a flow path member include a method of bringing the solid-phase reagent layer (or the release and solid-phase reagent layer) of the transfer medium for a testing device into contact with a flow path member to transfer the solid-phase reagent layer (or the release and solid-phase reagent layer) onto the flow path member.

A printer used for the thermal transfer is not particularly limited and may be appropriately selected depending on the intended purpose. Examples of the printer include thermal printers equipped with, for example, a serial thermal head and a line-type thermal head.

Energy applied for the thermal transfer is not particularly limited, may be appropriately selected depending on the intended purpose, and is lo preferably 0.05 mJ/dot or higher but 0.5 mJ/dot or lower. When the applied energy is 0.05 mJ/dot or higher, it is possible to efficiently melt the solid-phase reagent layer or the release and solid-phase reagent layer. When the applied energy is 0.5 mJ/dot or lower, it is possible to prevent the reagent from being thermally denatured. This prevents the support from being dissolved and the thermal head from being contaminated.

—Applications of Testing Device—

Applications of the testing device are not particularly limited and may be appropriately selected depending on the intended purpose. Examples of the applications of the testing device include biochemical sensors (sensing chips) for blood testing and DNA testing, and small-size analytical devices (chemical sensors) for, for example, quality control of foods and beverages.

Samples used in biochemical testings are not particularly limited and may be appropriately selected depending on the intended purpose. Examples of the samples include pathogens such as bacteria and viruses, blood, saliva, lesional tissues, etc. separated from living organisms, and excretion such as enteruria. For performing a prenatal diagnosis, the sample may be a part of a fetus cell in an amniotic fluid or a part of a dividing egg cell in a test tube. These samples may be condensed to a sediment directly or by, for example, centrifugation as needed and then subjected to a pre-treatment for cell destruction by, for example, an enzymatic treatment, a thermal treatment, a surfactant treatment, an ultrasonic treatment, and any combinations of these treatments.

The testing device of the present disclosure also has a function of chromatographing (separating or refining) the testing liquid because the flow path member functions as a static bed. In this case, the flow path member including the continuous cells of which internal wall has hydrophilicity functions as the static bed (or a support). Different components in the testing liquid flow through the flow path at different speeds because of the difference in the interaction with the static bed during the process of permeating the flow path, i.e., the difference in whether the components are hydrophilic or hydrophobic.

A component having a higher hydrophilicity adsorbs to the porous portion functioning as the static bed more easily, and repeats adsorbing and desorbing more times, resulting in a lower speed of permeation through the flow path. In contrast, a component having a higher hydrophobicity permeates the flow path without adsorbing to the static bed, and hence moves through the flow path more quickly. By extracting the target component in the testing liquid selectively based on the difference in the moving speed in the testing liquid and allowing the target component to undergo a reaction, it is possible to use the testing device as a highly functional chemical or biochemical sensor.

(Testing Method)

A testing method of the present disclosure includes a step of supplying a sample to the flow path member of the testing device of the present disclosure and a step of bringing the reagent formed as a solid phase over the resin layer into contact with the sample to release the reagent from the resin layer, preferably includes a step of making the reagent formed as a solid phase over the resin layer capture a portion of the sample, and further includes other steps as needed.

In a specific operation, the hydrophilic testing liquid 30 is dropped and supplied onto a dropping portion 12c (see FIG. 1) provided over the flow path member 12 of the testing device 10. Next, the supplied testing liquid 30 and the labeled antibody 16 formed as a solid phase over the resin layer 15a are brought into contact with each other, to release the labeled antibody 16 from the resin layer 15a. When any antigen 31 is contained in the testing liquid 30, the labeled antibody 16 released from the resin layer 15a reacts and binds with the antigen 31 (see FIG. 3).

Next, the testing liquid 30 containing the labeled antibody 16 and the antigen 31 spreads along the flow path member 12 and arrives at the region at which the resin layer 15b is disposed. The capture antibody 17 formed as a solid phase over the surface of the resin layer 15b facing the flow path member 12 also binds with and captures the antigen 31 that is in the state of being bound with the labeled antibody 16. The capture antibody 17 is formed as a solid phase over the resin layer 15b by the hydrophobic group 17g. Therefore, even when the capture antibody 17 contacts the testing liquid 30, the capture antibody 17 does not come to have affinity with the testing liquid 30 and is not easily released into the testing liquid 30. Even if some part of the capture antibody 17 is released into the testing liquid 30, the released part gets bound with the fiber constituting the flow path member 12 soon. This facilitates immobilization of the labeled antibody 16 to about the resin layer 15b, resulting in a clear color development on the test line (see FIG. 4A and FIG. 4B).

Any labeled antibody 16 that passes by the resin layer 15b without being captured spreads along the flow path member 12 and arrives at the region at which the resin layer 15c is disposed. In the present embodiment, the capture antibody 18 containing a hydrophobic group is formed as a solid phase over the surface of the resin layer 15c facing the flow path member 12. The labeled antibody 16 is captured by being bound with the capture antibody 18.

The capture antibody 18 is formed as a solid phase over the resin layer 15c by the hydrophobic group. Therefore, even when the capture antibody 18 contacts the testing liquid 30, the capture antibody 18 does not come to have affinity with the testing liquid 30 and is not easily released into the testing liquid 30. Even if some part of the capture antibody 18 is released into the testing liquid 30, the released part gets bound with the fiber constituting the flow path member 12 soon. This facilitates immobilization of the labeled antibody 16 to about the resin layer 15c, resulting in a clear color development on the control line (see FIG. 5A and FIG. 5B).

(Testing Kit)

A testing kit of the present disclosure includes the testing device of the present disclosure, and at least one selected from the group consisting of a sample picking unit configured to pick a sample and a liquid for treating the sample, and further includes other members as needed.

Figure 9:
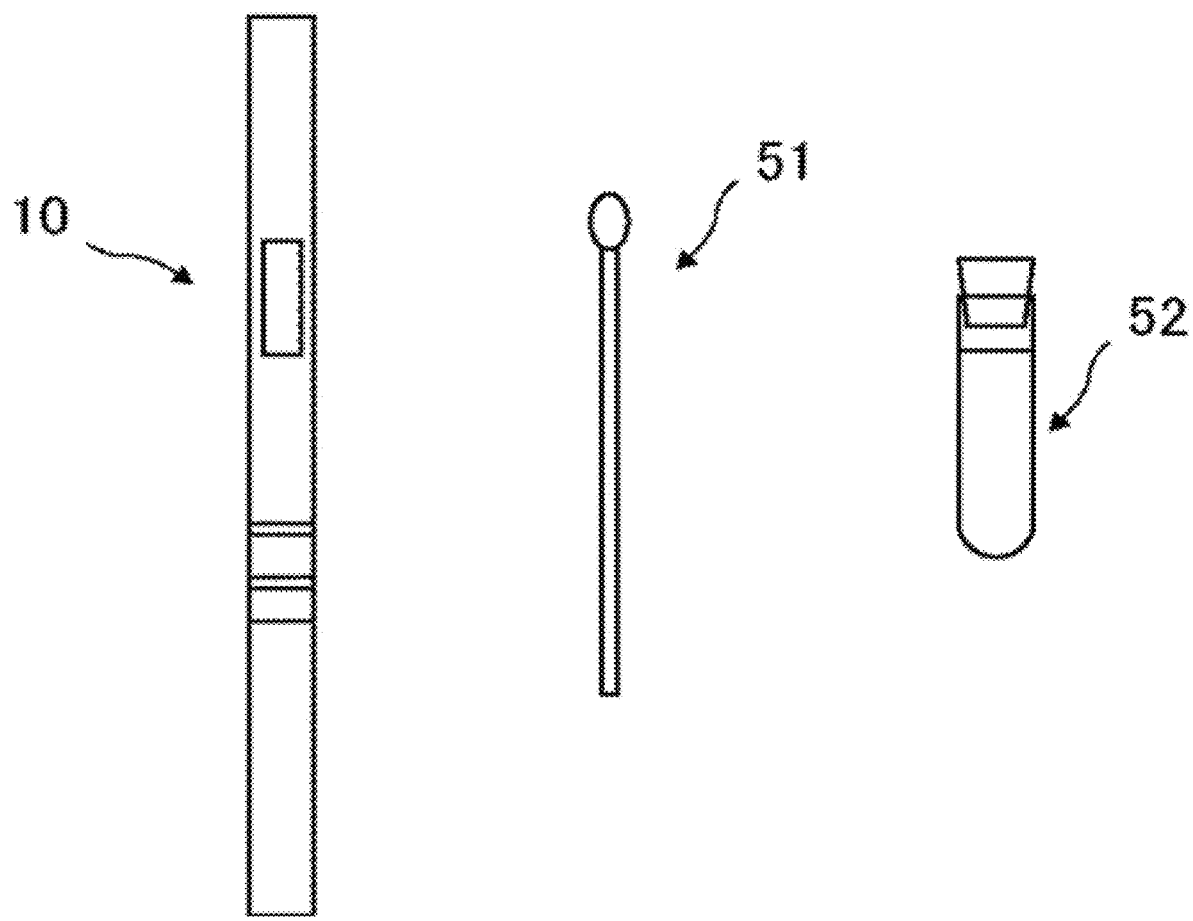
FIG. 9 is a schematic diagram illustrating an example of a testing kit of the present disclosure.

As illustrated in FIG. 9, the testing kit includes the testing device 10 of the present disclosure and at least one of a tool configured to pick a sample (an example of the sample picking unit) and a liquid for treating the sample.

Examples of the tool configured to pick a sample include a sterilized cotton swab 51 for picking a sample from, for example, pharynx or nasal cavity.

Examples of the liquid for treating the sample include a diluting fluid 52 for diluting the sample and an extraction liquid for extracting the sample.

Examples of the other members include an instruction manual.

In the embodiment described above, a case where the reagent formed as a solid phase over the resin layer 15 is an antigen or an o antibody is described. The present disclosure is not limited to this embodiment. The present disclosure can also be applied to, for example, a testing device using an indicator used in a chemical assay.

The indicator used in a chemical assay refers to a reagent for indicating a chemical property of a solution. The indicator is not particularly limited and may be appropriately selected depending on the intended purpose. Examples of the indicator include a pH indicator, various ionophores that discolor by reacting with various ions such as a lead ion, a copper ion, and a nitrite ion, and reagents that discolor by reacting with various agricultural chemicals.

In the embodiment described above, a case where the solid-phase reagent layer 103 or the release and solid-phase reagent layer 105 of the transfer medium 100 for a testing device is separated from the support 101 by heat during transfer is described. The present disclosure is not limited to this embodiment. For example, the solid-phase reagent layer 103 or the release and solid-phase reagent layer 105 may be separated from the support 101 by light. In this case, the release layer 102 or the release and solid-phase reagent layer 105 may contain a light absorber such as carbon black and may make the light absorber absorb light and generate heat, so that the release layer 102 or the release and solid-phase reagent layer 105 is fused to release the solid-phase reagent layer 103 or the release and solid-phase reagent layer 105. Alternatively, the release layer 102 or the release and solid-phase reagent layer 105 may contain a material that changes properties in response to light irradiation and may make the material absorb light, so that the release layer 102 is made fragile to release the solid-phase reagent layer 103 or the release and solid-phase reagent layer 105.

Examples of a transfer method other than the thermal transfer include a method of pasting a sheet formed of the solid-phase reagent layer 103 or the release and solid-phase reagent layer 105 over which the reagent is formed as a solid phase over the flow path member 12 by, for example, a tape.

In the embodiment described above, an example in which the flow path is formed throughout the flow path member 12 is described. The present disclosure is not limited to this embodiment. Examples of the method for forming a flow path in a partial region of the flow path member 12 include a method of forming a flow path wall defining an external edge of the flow path by filling the voids of the flow path member 12 with a hydrophobic material by a known method.

In the embodiment described above, an example in which the resin layers 15 are provided at a plurality of positions over the flow path member 12 is described. However, depending on the kind of the reagent, the resin layer 15 may be provided at one position over the flow path member 12. For example, a testing device capable of detecting a plurality of components at the same time can be obtained when the flow path member 12 that is provided with a resin layer 15a1 over which a reagent specifically bindable with a component A contained in the testing liquid 30 is formed as a solid phase and resin layers 15b1 and 15c1 over which reagents for capturing these reagent and component are formed as solid phases is further provided with a resin layer 15a2 over which a reagent specifically bindable with a component B contained in the testing liquid is formed as a solid phase and resin layers 15b2 and 15c2 over which reagents for capturing these reagent and component are formed as solid phases.

In the embodiment described above, an example in which the testing liquid 30 is hydrophilic is described. However, the testing liquid is not limited to a hydrophilic liquid. For example, the testing liquid 30 may be a solvophilic liquid containing an organic solvent such as alcohols such as methyl alcohol, ethyl alcohol, 1-propyl alcohol, and 2-propyl alcohol, and ketones such as acetone and methyl ethyl ketone (MEK). In this case, the term "hydrophilic" in the embodiment described above is replaced by "hydrophobic", and the term "hydrophobic" is replaced by "hydrophilic".

EXAMPLES

The present disclosure will be described by way of Examples. The present disclosure should not be construed as being limited to these Examples.

Preparation Example 1

—Preparation of Back Layer Coating Liquid—

A silicone-based rubber emulsion (with a solid concentration of 30% by mass) (16.8 parts by mass), a chloroplatinic acid catalyst (0.2 parts by mass), and toluene (83 parts by mass) were mixed, to prepare a back layer coating liquid of Preparation example 1.

Preparation Example 2

—Preparation of Release and Solid-phase Reagent Layer (For Immobilization) Coating Liquid—

A carnauba wax (90 parts by mass), an ethylene-vinyl acetate copolymer (1 part by mass), a styrene-butadiene rubber (4 parts by mass), a butadiene rubber (4 parts by mass), an acrylonitrile-butadiene rubber (1 part by mass), and a toluene/methyl ethyl ketone (at a ratio by volume of 7/3) solvent were mixed, to prepare a release and solid-phase reagent layer (for immobilization) coating liquid of Preparation example 2.

Preparation Example 3

—Preparation of Release and Solid-phase Reagent Layer (For Immobilization) Coating Liquid—

A polyethylene wax (14 parts by mass), an ethylene-vinyl acetate copolymer (6 parts by mass), toluene (60 parts by mass), and methyl ethyl ketone (20 parts by mass) were mixed, to prepare a release and solid-phase reagent layer (for immobilization) coating liquid of Preparation example 3.

Preparation Example 4

—Preparation of Solid-phase Reagent Layer (For Release) Coating Liquid—

A polyvinyl butyral resin (5 parts by mass) and ethanol (95 parts by mass) were mixed, to prepare a solid-phase reagent layer (for release) coating liquid of Preparation example 4.

Preparation Example 5

—Preparation of Test Line Reagent Coating Liquid—

As a diluting fluid, a Dulbecco's phosphate buffered saline (free of Ca and Mg, D-PBS (−), available from Nacalai Tesque, Inc., 14249-95) was added to an anti-rabbit IgG antibody (available from Sigma-Aldrich Co., LLC., R5506) to adjust the antibody concentration to 1,000 micrograms/mL, to prepare a test line reagent coating liquid of Preparation example 5.

Preparation Example 6

—Preparation of Control Line Reagent Coating Liquid—

As a diluting fluid, the D-PBS (−) mentioned above was added to rabbit IgG (available from Sigma-Aldrich Co., LLC., 15006) to be adjusted to 1,000 micrograms/mL, to prepare a control line reagent coating liquid of Preparation example 6.

Preparation Example 7

—Preparation of Labeled Antibody Reagent Coating Liquid—

A gold colloid-labeled anti-rabbit IgG antibody (available from BioAssay Works, LLC, Gold, with an average particle diameter of 40 nm and an optical density (OD)=15) was used as a labeled antibody reagent coating liquid of Preparation example 7.

Preparation Example 8

—Preparation of Test Line Reagent Coating Liquid—

As a diluting fluid, a Dulbecco's phosphate buffered saline (free of Ca and Mg, D-PBS (−), available from Nacalai Tesque, Inc., 14249-95) was added to an anti-hCG monoclonal antibody (available from Medix Biochemica Works, Ltd., anti-alpha subunit 6601 SPR-5) to be adjusted to 1,000 micrograms/mL, to prepare a test line reagent coating liquid of Preparation example 8.

Preparation Example 9

—Preparation of Control Line Reagent Coating Liquid—

As a diluting fluid, the D-PBS (−) mentioned above was added to an anti-mouse IgG antibody (available from Wako Pure Chemical Industries, Ltd., 566-70621) to be adjusted to 1,000 micrograms/mL, to prepare a control line reagent coating liquid of Preparation example 9.

Preparation Example 10

—Preparation of Labeled Antibody Reagent Coating Liquid—

A $KH_2PO_4$ buffer (with pH of 7.0) prepared to 50 mM (1 mL), and subsequently an anti-hCG monoclonal antibody (available from Medix Biochemica Inc., anti-hCG 5008 SP-5) prepared to 50 micrograms/mL (1 mL) were added to a gold colloid solution (available from BBI Solutions Inc., EMGC50, with a particle diameter of 50 nm) (9 mL) and stirred. The resultant was left to stand still for 10 minutes. To the resultant, a 1% by mass polyethylene glycol aqueous solution (available from Wako Pure Chemical Industries, Ltd., 168-11285) (550 microliters) was added and stirred, and then a 10% by mass BSA aqueous solution (available from Sigma-Aldrich Co., LLC., A-7906) (1.1 mL) was added and stirred.

Subsequently, this solution was centrifuged for 30 minutes. The supernatant was removed from this solution except for about 1 mL of the supernatant. The resultant solution was subjected to gold colloid re-dispersion with an ultrasonic cleaning machine. The centrifugation was performed with a centrifuge (available from Hitachi Koki Co., Ltd., HIMAC CF16RN) at a centrifugal acceleration of 8,000×g at 4 degrees C. Subsequently, the solution was dispersed in a gold colloid preservative solution (20 mM Tris-HCl buffer (with pH of 8.2), 0.05% by mass polyethylene glycol, 150 mM NaCl, a 1% by mass BSA aqueous solution, and a 0.1% by mass $NaN_3$ aqueous solution) (20 mL) and again centrifuged under the same conditions as described above. Subsequently, the supernatant was removed except for about 1 mL. The resultant solution was subjected to gold colloid re-dispersion with an ultrasonic cleaning machine. These operations were repeated to adjust the optical density (OD) of the gold colloid preservative solution to 15, to prepare a labeled antibody reagent coating liquid of Preparation example 10.

Example 1

<Production of Thermal Transfer Medium for Test Line>
—Formation of Back Layer—

The back layer coating liquid of Preparation example 1 was coated over one surface of a support, which was a polyethylene terephthalate (PET) film having an average thickness of 4.5 micrometers (available from Toray Industries, Inc., LUMIRROR F57), and dried at 80 degrees C. for 10 seconds, to form a back layer having an average thickness of 0.02 micrometers.

—Formation of Release and Solid-phase Reagent Layer (For Immobilization)—

Next, the release and solid-phase reagent layer (for immobilization) coating liquid of Preparation example 2 was coated over a surface of the PET film opposite to the surface over which the back layer was formed, and dried at 30 degrees C. for 10 minutes, to form a release and solid-phase reagent layer having an average thickness of 5.4 micrometers, an average void diameter of 0.29 micrometers, and a voidage of 27%.

—Production of Thermal Transfer Medium for Test Line—

The product obtained by laminating the back layer and the release and solid-phase reagent layer over the PET film was cut into a strip shape of 1 cm×3 cm. The strip was put in the center of a glass dish having an internal diameter of 5 cm and a depth of 1 cm in a manner that the back layer of the PET film had contact with the dish. Cubic blocks formed of SUS and having a dimension of 1 cm on each side were put on both ends of the film to press the film from above. Next, the test line reagent coating liquid of Preparation example 5 was calmly poured into the dish such that the liquid height would be 1.5 mm. The dish was put in a pressure vessel (TM5SRV, available from Unicontrols Co., Ltd.) to perform pressurization with a compressor (model No. DP-40C-AC100V, available from VACUTRONICS Inc.) until the gauge pressure of the pressure vessel became 4.5 MPa. The PET film was left to stand still for 10 minutes while being kept in the pressurized state and then returned to the atmospheric pressure. In this way, the reagent was formed as a solid phase.

After formation of the solid phase was completed, the film over which the solid phase was formed was taken out from the dish, and pasted over a shaker (SHAKE-XR mounted with WR-3636, both available from Taitec Corporation) in a manner that the surface over which the solid phase was formed faced outside. Distilled water was poured onto the surface over which the solid phase was formed in an amount of 100 microliters per unit area (cm$^2$) of the surface, and then the film was gently shaken at 25 degrees C. at a shaking speed of 20 r/min for 1 minute, to sufficiently drain and clean the film of any excessive coating liquid.

After cleaning, the film as is was dried in a dessicator having a temperature of 25 degrees C. and a relative humidity of 20% for 15 minutes, to complete formation of the reagent as a solid phase over the release and solid-phase reagent layer (for immobilization). In the way described above, a thermal transfer medium for a test line of Example 1 was obtained.

—Production of Thermal Transfer Medium for Control Line—

A thermal transfer medium for a control line of Example 1 was obtained in the same manner as in the production of the thermal transfer medium for a test line described above, except that the test line reagent coating liquid of Preparation example 5 used in the production of the thermal transfer medium for a test line was changed to the control line reagent coating liquid of Preparation example 6.

<Production of Thermal Transfer Medium for Labeled Antibody>

A back layer was formed over one surface of a support, which was a polyethylene terephthalate (PET) film having an average thickness of 4.5 micrometers (LUMIRROR F57, available from Toray Industries, Inc.) in the same manner as in the production of the thermal transfer medium for a test line described above. Next, the release and solid-phase reagent layer (for immobilization) coating liquid of Preparation example 2 was coated and dried at 40 degrees C. for 10 minutes, to form a release and solid-phase reagent layer having an average thickness of 1.8 micrometers. Further, the solid-phase reagent layer (for release) coating liquid of Preparation example 4 was coated over the release and solid-phase reagent layer (for immobilization) and dried at 30 degrees C. for 10 minutes, to form a solid-phase reagent layer (for release) having an average thickness of 5 micrometers.

Furthermore, the labeled antibody reagent coating liquid of Preparation example 7 was coated over the solid phase reagent layer (for release) in an amount of 25 microliters/cm$^2$ and dried in a vacuum dryer at 25 degrees C. for 5 hours, to form the reagent as a solid phase over the solid-phase reagent layer (for release). In the way described above, a thermal transfer medium for a labeled antibody of Example 1 was obtained.

<Production of Testing Device>

Figure 10A:
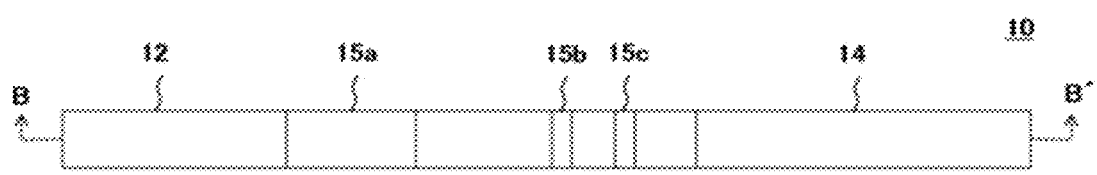
FIG. 10A is a top view illustrating an example of a testing device used in Example.
Figure 10B:
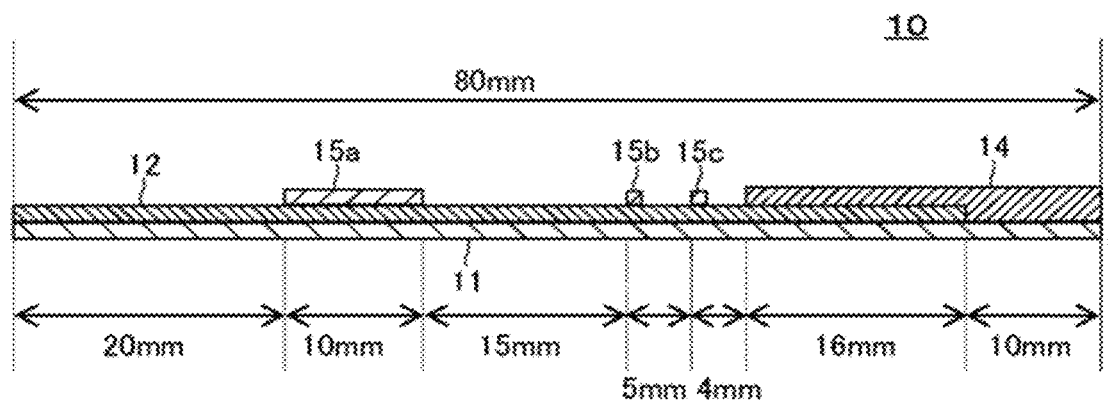
FIG. 10B is a cross-sectional view of FIG. 10A taken along B-B'.

In the way described below, a testing device illustrated in FIG. 10A and FIG. 10B was produced. FIG. 10A is a top view illustrating an example of a testing device used in Examples. FIG. 10B is a cross-sectional view of FIG. 10A taken along B-B'.

—Production of Paper Substrate—

As a thermoplastic resin, a polyester-based hot-melt adhesive (available from Toagosei Co., Ltd., ARONMELT PES375S40) was heated to 190 degrees C., and then with a roll coater, coated over a PET film (available from Toray Industries, Inc., LUMIRROR S10, with an average thickness of 50 micrometers) 11 cut into a size of 40 mm in width and 80 mm in length, to have an average thickness of 50 micrometers over the PET film, to form an adhesive layer.

The PET film 11 over which the adhesive layer was formed was left to stand still for 2 hours or longer. Subsequently, a nitrocellulose membrane (available from Merck Millipore Corporation, HF180, with a voidage of 70%) cut into a size of 40 mm in width and 70 mm in length was overlapped over the adhesive layer-coated surface in a manner that one end of the adhesive layer-coated surface in the longer direction and one end of each member in the longer direction (this end is referred to as upstream end, and the opposite end is referred to as downstream end) would coincide with each other, and a load of 1 kgf/cm$^2$ was applied to the overlapped members at a temperature of 150 degrees C. for 10 seconds. Finally, the obtained product was cut along the longer direction into a size of 4 mm in width and 80 mm in length, to obtain a paper substrate 12.

The voidage of the paper substrate 12 was calculated according to a calculation formula 1 below based on the basis weight (g/m$^2$) of the paper substrate 12, the average thickness (micrometer) of the paper substrate 12, and the specific gravity of the component of the paper substrate 12. As a result, the voidage of the paper substrate was 70%. A paper substrate having a voidage of 40% or higher but 90% or lower can be said to be a porous paper substrate.

Voidage (%)={1−[basis weight (g/m$^2$)/average thickness (micrometer)/specific gravity of the component]}×100     [Calculation formula 1]

—Transfer of Labeled Antibody—

The paper substrate 12 and the surface of the thermal transfer medium for a labeled antibody having the reagent formed as a solid phase were faced and overlapped with each other. Subsequently, with a thermal transfer printer, the thermal transfer medium for a labeled antibody was transferred in a pattern of 4 mm in width and 10 mm in length (resin layer 15a) onto the paper substrate 12 at a position away from the upstream end by 20 mm, as illustrated in FIG. 10A and FIG. 10B.

The thermal transfer printer was equipped with a thermal head having a dot density of 300 dpi (available from TDK Corporation), and constructed as an evaluation system having a printing speed of 8.7 mm/sec and an applied energy of 0.28 mJ/dot.

—Transfer of Test Line and Control Line—

As illustrated in FIG. 10A and FIG. 10B, the thermal transfer medium for a test line was transferred in a line shape of 4 mm in width and 0.8 mm in length to a position that was away by 15 mm from the position to which the thermal transfer medium for a labeled antibody was transferred. Then, the thermal transfer medium for a control line was transferred in a line shape of 4 mm in width and 0.8 mm in length to a position that was away by 5 mm from the position to which the thermal transfer medium for a test line was transferred. The lines were formed under the same printing conditions as used in Transfer of labeled antibody described above.

—Production of Absorbing Member—

An absorbing member 14 (available from Merck Millipore Corporation, SUREWICK C248) was provided as illustrated in FIG. 10A and FIG. 10B, to obtain an immunochromatoassay (testing device 10) of Example 1.

Next, the voidage of the release and solid-phase reagent layer before formation of the reagent as a solid phase, the average void dimeter of the release and solid-phase reagent layer before formation of the reagent as a solid phase, the average thickness of the release and solid-phase reagent layer before formation of the reagent as a solid phase, and the contact angle of the release and solid-phase reagent layer coating liquid were measured according to the methods described below. The results are presented in Table 1-1.

<Voidage>

First, with a scanning electron microscope (SEM), a cross-section of the release and solid-phase reagent layer before formation of the reagent as a solid phase was magnified at a magnification of ×5,000 and recorded in the form of a digital image. Next, with image processing software (e.g., IMAGE J), image processing was performed to monochromatize the digital image and binarize the digital image with setting of a threshold such that void regions would be extracted from the cross-section of the release and solid-phase reagent layer before formation of the reagent as a solid phase. Finally, the area of the void regions in an arbitrary region and the area of the cross-section of the material were calculated, to obtain the voidage according to a mathematical formula 2 below.

Voidage (%)=(area of the void regions)/(area of the whole release and solid-phase reagent layer)×100  [Mathematical formula 2]

<Average Void Diameter>

The average void diameter of the release and solid-phase reagent layer before formation of the reagent as a solid phase was calculated as an average of void diameter measurements of arbitrary 10 voids extracted from the digital image of the cross-section of the release and solid-phase reagent layer obtained in the calculation of the voidage.

<Average Thickness>

The average thickness of the release and solid-phase reagent layer before formation of the reagent as a solid phase was calculated as an average of thicknesses measured with a micrometer (MDH-25M available from Mitutoyo Corporation) at a total of 15 positions of the measuring target, namely 5 positions in the longer direction (direction of length)×3 positions in the width direction that were selected at approximately equal intervals.

<Measurement of Contact Angle (Evaluation of Hydrophilicity/Hydrophobicity)>

A PET film was smoothly coated with the release and solid-phase reagent layer coating liquid of Preparation example 2 with a bar coater such that an average thickness would be 5.4 micrometers, and then compressed and smoothed with a press machine, to obtain a release and solid-phase reagent layer. Distilled water was dropped onto a surface of the release and solid-phase reagent layer in an amount of 4.0 microliters to measure contact angles at arbitrary 5 points on the surface of the sample with a portable contact angle meter (PG-X, available from Fibro System AB) in an environment of 25 degrees C. and −50% RH. The average was calculated, to evaluate hydrophilicity/hydrophobicity according to the criteria described below.

[Evaluation Criteria]

"Hydrophilicity": The contact angle with respect to distilled water was less than 75 degrees.

"Hydrophobicity": The contact angle with respect to distilled water was 75 degrees or greater.

<Evaluation of Line>

—Preparation of Testing Liquid—

As a carrier liquid, a D-PBS (−) solution of 0.3% by mass TWEEN 20 (available from Sigma-Aldrich Co., LLC., P9416-50ML) was prepared.

Next, the carrier liquid was added to rabbit IgG, to obtain a testing liquid prepared to a concentration of 500 ng/mL.

—Reaction—

The testing liquid (100 microliters) was dropped onto the upstream end of the immunochromatoassay illustrated in FIG. 10A and FIG. 10B, to observe the state of spreading of the testing liquid.

—Measurement of Color Developing Density of Line—

The immunochromatoassay in which a reaction was completed was stored in a housing case for measurement, and a reading was measured with an immunochromatoreader (C10066, available from Hamamatsu Photonics K.K.), to evaluate the color developing density on the line according to the criteria described below. The result is presented in Table 1. A higher reading is more preferable, because the color developing density on the line was higher.

[Evaluation Criteria]

A: The reading was 300 or higher.

B: The reading was 200 or higher but lower than 300.

C: The reading was lower than 200 or unmeasurable because there was no observable line.

Example 2

Unlike in the step of forming a release and solid-phase reagent layer (for immobilization) in <Production of thermal transfer medium for test line> of Example 1, a release and solid-phase reagent layer (for immobilization) having an average thickness of 9.0 micrometers, an average void diameter of 0.27 micrometers, and a voidage of 21% was formed.

Unlike in the step of forming a release and solid-phase reagent layer (for immobilization) in <Production of thermal transfer medium for control line> of Example 1, a release and solid-phase reagent layer was formed to have an average thickness of 7.2 micrometers instead of 5.4 micrometers.

An immunochromatoassay (testing device 10) of Example 2 was produced in the same manner as in Example 1 except the steps described above, and evaluated in the same manners as in Example 1. The results are presented in Table 1-1 and Table 1-2.

Example 3

A thermal transfer medium for a test line was produced in the same manner as in Example 1, except that unlike in the step of forming a release and solid-phase reagent layer (for immobilization) in <Production of thermal transfer medium for test line> of Example 1, the release and solid-phase reagent layer (for immobilization) coating liquid of Preparation example 2 was changed to the release and solid-phase reagent layer (for immobilization) coating liquid of Preparation example 3, and a release and solid-phase reagent layer (for immobilization) having an average thickness of 5.4 micrometers, an average void diameter of 0.32 micrometers, and a voidage of 29% was formed.

In addition, a thermal transfer medium for a control line was produced in the same manner as in Example 1, except that unlike in the step of forming a release and solid-phase reagent layer (for immobilization) in <Production of thermal transfer medium for control line> of Example 1, the release and solid-phase reagent layer (for immobilization) coating liquid of Preparation example 2 was likewise changed to the release and solid-phase reagent layer (for immobilization) coating liquid of Preparation example 3.

An immunochromatoassay (testing device 10) of Example 3 was produced in the same manner as in Example 1 except the steps described above, and evaluated in the same manners as in Example 1. The results are presented in Table 1-1 and Table 1-2.

Example 4

A testing device was produced in the same manner as in Example 1, except that unlike in Example 1, the test line reagent coating liquid of Preparation example 5 was changed to the test line reagent coating liquid of Preparation example 8, the control line reagent coating liquid of Preparation example 6 was changed to the control line reagent coating liquid of Preparation example 9, and the labeled antibody reagent coating liquid of Preparation example 7 was changed to the labeled antibody reagent coating liquid of Preparation example 10.
<Evaluation of Line>
—Preparation of Testing Liquid—
As a carrier liquid, a /D-PBS (−) solution of 0.3% by mass TWEEN 20 (available from Sigma-Aldrich Co., LLC., P9416-50ML) was prepared.

Next, the carrier liquid was added to hCG (available from R&D Systems Inc., RECOMBINANT HCG, 7727-CG-010) to be prepared to 500 mIU/mL, to obtain a testing liquid.
—Reaction—
The testing liquid (100 microliters) was dropped onto the upstream end of the immunochromatoassay. Fifteen minutes later, the immunochromatoassay of Example 4 was observed.

Next, the immunochromatoassay (testing device 10) obtained in Example 4 was evaluated in the same manners as in Example 1. The results are presented in Table 1-1 and Table 1-2.

Example 5

Unlike in the step of transferring a test line and a control line in <Production of testing device> of Example 1, instead of performing transfer with a thermal transfer printer, the thermal transfer medium for a test line was cut into a line shape of 4 mm in width and 0.8 mm in length, to produce a film for a test line. Further, the surface of the film for a test line having the reagent formed as a solid phase was faced and overlapped with a paper substrate.

Next, an adhesive tape (available from 3M Japan Limited, SCOTCH MENDING TAPE 810-1-18) cut into a line shape of 4 mm in width and 3.0 mm in length was pasted to cover the film for a test line in a manner that the center lines of the film for a test line and the adhesive tape in the longer direction would coincide with each other, to form a test line 15b. In the same manner, a control line 15c was formed by pasting a control line with the use of the adhesive tape.

An immunochromatoasay (testing device 10) of Example 5 was produced in the same manner as in Example 1 except the change to the above-described steps in Example 1, and evaluated in the same manners as in Example 1. The results are presented in Table 1-1 and Table 1-2.

Example 6

Figure 11A:
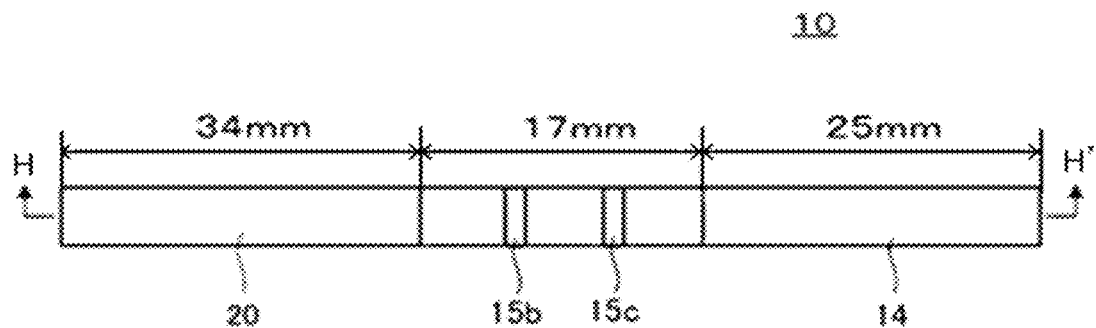
FIG. 11A is a top view illustrating another example of a testing device used in Example.
Figure 11B:
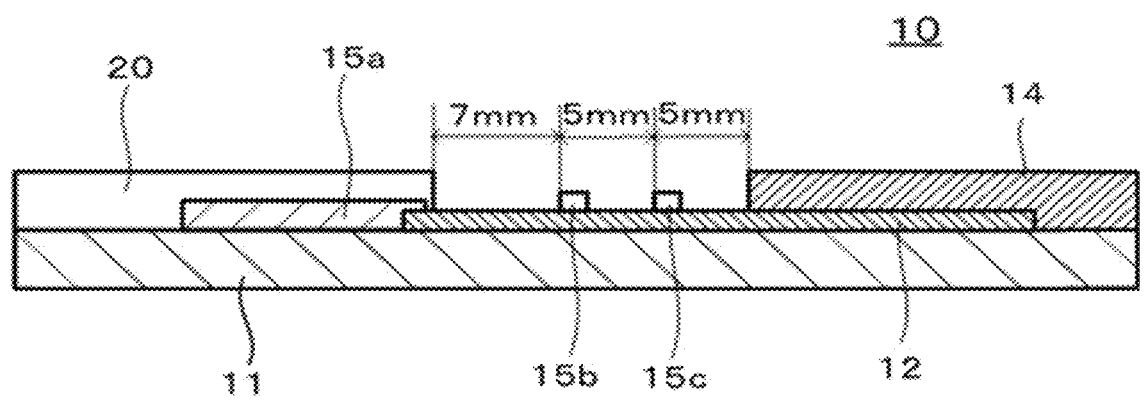
FIG. 11B is a cross-sectional view of FIG. 11A taken along H-H'.

Unlike in the step of producing a testing device of Example 1, instead of producing a paper substrate of Example 1, a test strip was produced according to the procedure described below.
<Production of Test Strip>
—Production of Labeled Antibody Support Pad—
As a gold colloid-labeled antibody, a gold colloid-labeled anti-rabbit IgG antibody (available from BioAssay Works, LLC, Gold, with an average particle diameter of 40 nm and OD=15) was coated in an amount of 25 microliters/cm² over a glass fiber pad (GFCP203000, available from Merck Millipore Corporation) cut into a size of 3.5 mm in width and 16 mm in length, and dried under reduced pressure for 5 hours, to produce a labeled antibody support pad.
—Formation of Test Line and Control Line—
Next, in the same manner as in Example 1, a test line 15b and a control line 15c were formed at the positions indicated in FIG. 11A and FIG. 11B over a nitrocellulose membrane filter (HF180, available from Merck Millipore Corporation, with a voidage of 70%) cut into a size of 3.5 mm in width and 38 mm in length.
—Assembling—
As illustrated in FIG. 11A and FIG. 11B, the nitrocellulose membrane filter 12 over which the test line 15b and the control line 15c were formed was bonded over a PET film (LUMIRROR S10, available from Toray Industries, Inc., with an average thickness of 100 micrometers) 11, which was cut into a size of 3.5 mm in width and 76 mm in length, at a position that was away by 32 mm from one end of the PET film 11 in the loner direction in a manner that a surface of the nitrocellulose membrane filter 12 opposite to the reagent-coated surface faced the PET film 11.

Next, the labeled antibody support pad 15a produced above was is disposed over the top surface of the nitrocellulose membrane filter 12 in a manner to overlap the upstream end of the nitrocellulose membrane filter by 2 mm and pasted at the position. Furthermore, a sample pad having a size of 3.5 mm in width and 34 mm in length (available from Asahikasei Fibers Corporation, BEMCOT M-3II) was disposed in a manner to overlap the top surface of the labeled antibody support pad by 16 mm and pasted at the position, to produce a sample dropping pad 20.

Next, as an absorbing member 14, an absorbing pad having a size of 3.5 mm in width and 25 mm in length (available from Merck Millipore Corporation, SUREWICK C248) was disposed over the top surface of the nitrocellulose membrane filter 12 in a manner to overlap the downstream end of the PET film 11 by 19 mm and pasted at the position, to obtain a test strip.
—Housing—
The test strip was stored in a housing case for measurement, to obtain an immunochromatoassay (testing device 10) of Example 6.
—Evaluation—
The immunochromatoassay (testing device 10) produced in Example 6 was evaluated in the same manners as in Example 1. The results are presented in Table 1-1 and Table 1-2.

Comparative Example 1

Unlike in —Production of thermal transfer medium for test line— in <Production of thermal transfer medium for test line> of Example 1, an antibody was formed as a solid phase by the following method that involved no pressurization during formation of the antibody as a solid phase.

—Production of Thermal Transfer Medium for Test Line—

The product produced in Example 1 by laminating the back layer and release and solid-phase reagent layer over the PET film was cut into a strip shape of 1 cm×3 cm. The test line reagent coating liquid of Preparation example 4 was coated over the release and solid-phase reagent layer in an amount of 12 microliters per unit area (cm$^2$), and then the resultant cut film was left to stand still at 25 degrees C. for 10 minutes in a container kept to a relative humidity of 80% so as not for the coating liquid to dry. After standing-still, the cut film was pasted over a shaker (SHAKE-XR mounted with WR-3636, both available from Taitec Corporation) in a manner that the surface over which the reagent was formed as a solid phase faced outside. Distilled water was poured onto the surface over which the solid phase was formed in an amount of 100 microliters per unit area (cm$^2$) of the surface, and then the film was gently shaken at 25 degrees C. at a shaking speed of 20 r/min for 1 minute. After shaking was completed, the film was removed, drained of any water remaining over the surface, and dried in a dessicator having a temperature of 25 degrees C. and a relative humidity of 20% for 15 minutes, to complete formation of the reagent as a solid phase over the release and solid-phase reagent layer (for immobilization). In the way described above, a thermal transfer medium for a test line of Comparative Example 1 was obtained.

An immunochromatoassay (testing device 10) of Comparative Example 1 was produced in the same manner as in Example 1 except the change to the above-described step in Example 1, and evaluated in the same manners as in Example 1. The results are presented in Table 1-1 and Table 1-2.

Comparative Example 2

Unlike in the step of forming a release and solid-phase reagent layer (for immobilization) in <Production of thermal transfer medium for test line> of Example 1, the conditions for drying performed after the release and solid-phase reagent layer (for immobilization) coating liquid of Preparation example 2 was coated was set to drying at 40 degrees C. for 10 minutes instead of drying at 30 degrees C. for 10 minutes, to form a release and solid-phase reagent layer (for immobilization) having an average thickness of 5.4 micrometers, an average void diameter of 0 micrometers, and a voidage of 0%.

A cross-section of the release and solid-phase reagent layer was observed with a SEM, and it was confirmed that the release and solid-phase reagent layer was substantially a non-porous body.

—Production of Thermal Transfer Medium for Test Line—

Next, a product obtained by laminating a back layer and a release and solid-phase reagent layer over a PET film was cut into a strip shape of 1 cm×3 cm. The test line reagent coating liquid of Preparation example 4 was coated over the release and solid-phase reagent layer in an amount of 12 microliters per unit area (cm$^2$), and the resultant cut film was left to stand still at 25 degrees C. for 10 minutes in a container kept to a relative humidity of 80% so as not for the coating liquid to dry. After standing-still, the cut film was pasted over a shaker (SHAKE-XR mounted with WR-3636, both available from Taitec Corporation) in a manner that the surface over which the reagent was formed as a solid phase faced outside. Distilled water was poured onto the surface over which the solid phase was formed in an amount of 100 microliters per unit area (cm$^2$) of the surface, and then the film was gently shaken at 25 degrees C. at a shaking speed of 20 r/min for 1 minute. After shaking was completed, the film was removed, sufficiently drained of any water remaining over the surface, and dried in a dessicator having a temperature of 25 degrees C. and a relative humidity of 20% for 15 minutes, to complete formation of the reagent as a solid phase over the release and solid-phase reagent layer (for immobilization). In the way described above, a thermal transfer medium for a test line of Comparative Example 2 was obtained.

An immunochromatoassay (testing device 10) of Comparative Example 2 was produced in the same manner as in Example 1 except the change to the above-described step in Example 1, and evaluated in the same manners as in Example 1. The results are presented in Table 1-1 and Table 1-2.

Comparative Example 3

Unlike in the step of forming a release and solid-phase reagent layer (for immobilization) in <Production of thermal transfer medium for test line> of Example 1, a change was made to obtain a release and solid-phase reagent layer having an average thickness of 20.0 micrometers, and the condition for drying performed after coating was set to drying at 40 degrees C. for 10 minutes instead of drying at 30 degrees C. for 10 minutes, to form a release and solid-phase reagent layer (for immobilization) having an average thickness of 20.0 micrometers, an average void diameter of 0 micrometers, and a voidage of 0%.

A cross-section of the release and solid-phase reagent layer was observed with a SEM, and it was confirmed that the release and solid-phase reagent layer was substantially a non-porous body.

—Production of Thermal Transfer Medium for Test Line—

Next, a product obtained by laminating a back layer and the release and solid-phase reagent layer over a PET film was cut into a strip shape of 1 cm×3 cm. The test line reagent coating liquid of Preparation example 4 was coated over the release and solid-phase reagent layer in an amount of 12 microliters per unit area (cm$^2$), and the resultant cut film was left to stand still at 25 degrees C. for 10 minutes in a container kept to a relative humidity of 80% so as not for the coating liquid to dry. After standing-still, the cut film was pasted over a shaker (SHAKE-XR mounted with WR-3636, both available from Taitec Corporation) in a manner that the surface over which the reagent was formed as a solid phase faced outside. Distilled water was poured onto the surface over which the solid phase was formed in an amount of 100 microliters per unit area (cm$^2$) of the surface, and then the film was gently shaken at 25 degrees C. at a shaking speed of 20 r/min for 1 minute. After shaking was completed, the film was removed, sufficiently drained of any water remaining over the surface, and dried in a dessicator having a temperature of 25 degrees C. and a relative humidity of 20% for 15 minutes, to complete formation of the reagent as a solid phase over the release and solid-phase reagent layer (for immobilization). In the way described above, a thermal transfer medium for a test line of Comparative Example 3 was obtained.

An immunochromatoassay (testing device 10) of Comparative Example 3 was produced in the same manner as in Example 1 except the change to the above-described step in Example 1, and evaluated in the same manners as in Example 1. The results are presented in Table 1-1 and Table 1-2.

Comparative Example 4

The steps of forming a test line and a control line in Example 1 were changed to the steps described below, to form the lines.

As a hydrophilic porous body, a product obtained by forming glass fiber (GFDX10300, available from Merck Millipore Corporation) into a form of a thin film and compressing the thin film with a press machine was cut into a strip shape of 1 cm×3 cm. The strip was put in the center of a glass dish having an internal diameter of 5 cm and a depth of 1 cm. Cubic blocks formed of SUS and having a dimension of 1 cm on each side were put on both ends of the glass fiber to press the glass fiber from above.

Next, the test line reagent coating liquid of Preparation example 5 was calmly poured into the dish such that the liquid height would be 1.5 mm. The dish was put in a pressure vessel (TM5SRV, available from Unicontrols Co., Ltd.) to perform pressurization with a compressor (model No. DP-40C-AC100V, available from VACUTRONICS Inc.) until the gauge pressure of the pressure vessel became 4.5 MPa. The strip was left to stand still for 10 minutes while being kept in the pressurized state and then returned to the atmospheric pressure. In this way, the reagent was formed as a solid phase.

After formation of the solid phase was completed, the glass fiber over which the solid phase was formed was taken out from the dish, and pasted over a shaker (SHAKE-XR mounted with WR-3636, both available from Taitec Corporation). Distilled water was poured onto the surface over which the solid phase was formed in an amount of 100 microliters per unit area (cm$^2$) of the surface, and then the glass fiber was gently shaken at 25 degrees C. at a shaking speed of 20 r/min for 1 minute. After shaking, the glass fiber as is was dried in a dessicator having a temperature of 25 degrees C. and a relative humidity of 20% for 15 minutes, to complete formation of the reagent as a solid phase.

Next, an adhesive tape (available from 3M Japan Limited, SCOTCH MENDING TAPE 810-1-18) was cut into a strip shape of 4 mm in length and 3.0 mm in width. The center lines of the glass fiber and the adhesive tape in the longer direction were brought to coincide with each other, and the glass fiber was pasted over a paper substrate 12 with the adhesive tape in a manner that the glass fiber and the paper substrate 12 would face each other. In this way, a test line 15*b* was formed. The position of the test line 15*b* was the same as in Example 1.

A control line 15*c* was formed in the same manner as in Example 1, except that in the step described immediately above, the test line reagent coating liquid of Preparation example 5 was changed to the control line reagent coating liquid of Preparation example 6.

An immunochromatoassay (testing device 10) of Comparative Example 4 was produced in the same manner as in Example 1, except that the steps for forming a test line and a control line were changed from Example 1.

For evaluation of hydrophilicity/hydrophobicity of the glass fiber, a sample was prepared by compressing and smoothing a glass fiber alone with a press machine. A liquid droplet of distilled water was caused to land onto the sample, and a contact angle of the liquid droplet 13 msec later was used. Here, the contact angle was 17 degrees.

Literature values for contact angles of the glass material in a bulk state were from 16 degrees through 35 degrees, all of which were 75 degrees or less (see "Physical chemistry on glass surface, authored by Shoji Dobashi" and "Kodansha Ltd., Super-water-repellency/super hydrophilicity technology in electronic/energy fields, Takashi Murata, Nozomi Asai, planning and editing, Technical Information Institute Co., Ltd."). In the other respects, the same evaluations as in Example 1 were performed. The results are presented in Table 1-1 and Table 1-2.

TABLE 1-1

| | | Test line (release and solid-phase reagent layer) | | | | | | |
|---|---|---|---|---|---|---|---|---|
| | | Contact angle (degree) | Hydrophilicity/ hydrophobicity | Voidage (%) | Average void diameter (micrometer) | Average thickness (micrometer) | Condition for drying test line | |
| | Material | | | | | | Temperature | Time |
| Ex. 1 | Preparation example 2 | 92 | Hydrophobic | 27 | 0.29 | 5.4 | 30 degrees C. | 10 min |
| Ex. 2 | Preparation example 2 | 92 | Hydrophobic | 21 | 0.27 | 9.0 | 30 degrees C. | 10 min |
| Ex. 3 | Preparation example 3 | 106 | Hydrophobic | 29 | 0.32 | 5.4 | 30 degrees C. | 10 min |
| Ex. 4 | Preparation example 2 | 92 | Hydrophobic | 27 | 0.29 | 5.4 | 30 degrees C. | 10 min |
| Ex. 5 | Preparation example 2 | 92 | Hydrophobic | 27 | 0.29 | 5.4 | 30 degrees C. | 10 min |
| Ex. 6 | Preparation example 2 | 92 | Hydrophobic | 27 | 0.29 | 5.4 | 30 degrees C. | 10 min |
| Comp. Ex. 1 | Preparation example 2 | 92 | Hydrophobic | 27 | 0.29 | 5.4 | 40 degrees C. | 10 min |
| Comp. Ex. 2 | Preparation example 2 | 92 | Hydrophobic | 0 | 0 | 5.4 | 40 degrees C. | 10 min |
| Comp. Ex. 3 | Preparation example 2 | 92 | Hydrophobic | 0 | 0 | 20.0 | 40 degrees C. | 10 min |
| Comp. Ex. 4 | Glass fiber | 17 | Hydrophilic | 89 | — | 97.3 | — | — |

TABLE 1-2

|  | Method for forming reagent as solid phase | Color developing density | |
|---|---|---|---|
|  |  | Reading by reader | Evaluation of rank |
| Ex. 1 | With pressurization | 411 | A |
| Ex. 2 | With pressurization | 513 | A |
| Ex. 3 | With pressurization | 409 | A |
| Ex. 4 | With pressurization | 382 | A |
| Ex. 5 | With pressurization | 420 | A |
| Ex. 6 | With pressurization | 423 | A |
| Comp. Ex. 1 | Without pressurization | 203 | B |
| Comp. Ex. 2 | Without pressurization | 212 | B |
| Comp. Ex. 3 | Without pressurization | 215 | B |
| Comp. Ex. 4 | With pressurization | 158 | C |

From the results of Table 1-1 and Table 1-2, in Examples 1 to 6, it was possible to confirm a high color developing density, because the test line was formed of a porous body formed of a hydrophobic material.

In contrast, in Comparative Example 1, the antibody coating liquid was not able to reach inside the voids of the resin layer because air was remaining in the voids during formation of the antibody as a solid phase. Hence, in the resin layer of Comparative Example 1, it was able to form the antibody as a solid phase only to a region about the surface of the resin layer the antibody coating liquid was able to have contact with, resulting in a low amount of solid phase of the antibody, and hence a low color developing density on the test line.

In Comparative Examples 2 and 3, the resin layer was substantially free of voids, resulting in a small specific surface area over which the antibody was formed as a solid phase, and hence a low color developing density on the test line.

In Comparative Example 4, the material constituting the test line was hydrophilic, resulting in a weak hydrophobic interaction between the antibody and the material, and hence an insufficient color development.

The embodiments of the present disclosure are, for example, as follows:
<1> A testing device including:
a porous flow path member in which a flow path for flowing a sample is formed; and
a resin layer provided at at least one position over the flow path member,
wherein the resin layer is a porous body formed of a hydrophobic material, and
wherein a reagent reactive with the sample is formed as a solid phase over a surface of the resin layer facing the flow path member and inside voids of the resin layer.
<2> The testing device according to <1>,
wherein the material constituting the resin layer has a contact angle of 75 degrees or greater with respect to distilled water at 25 degrees C.
<3> The testing device according to <1> or <2>,
wherein voidage of the resin layer before formation of the reagent as the solid phase is 10% or higher but 45% or lower.
<4> The testing device according to any one of <1> to <3>,
wherein the resin layer contains a water-insoluble resin.
<5> The testing device according to any one of <1> to <4>,
wherein the testing device includes the porous flow path member in which a flow path for flowing a sample is formed,
wherein the resin layer includes a first resin layer and a second resin is layer that are provided over the flow path member,
wherein the first resin layer is a porous body formed of a hydrophobic material,
wherein the first resin layer includes at least a capture antibody over a surface of the first resin layer facing the flow path member and inside voids of the first resin layer, and
wherein the second resin layer includes a labeled antibody over a surface of the second resin layer facing the flow path member.
<6> The testing device according to <5>,
wherein the material constituting the first resin layer has a contact angle of 75 degrees or greater with respect to distilled water at 25 degrees C.
<7> The testing device according to <5> or <6>,
wherein voidage of the first resin layer before formation of the solid phase is 10% or higher but 45% or lower.
<8> The testing device according to any one of <5> to <7>,
wherein the first resin layer includes a plurality of first resin layers.
<9> The testing device according to any one of <5> to <8>,
wherein the first resin layer contains a resin containing a hydrophobic group.
<10> The testing device according to <9>,
wherein the resin containing a hydrophobic group is any one of a hydrophobic resin and a first amphiphilic resin.
<11> The testing device according to any one of <5> to <10>,
wherein the second resin layer contains a second amphiphilic resin.
<12> The testing device according to <11>,
wherein the first amphiphilic resin is a resin that contains more hydrophobic groups than the second amphiphilic resin contains.
<13> The testing device according to any one of <5> to <12>,
wherein the first resin layer contains a water-insoluble resin.
<14> A testing kit including:
the testing device according to any one of <1> to <13>; and
at least one selected from the group consisting of a sample picking unit configured to pick a sample and a liquid for treating the sample.
<15> A transfer medium for a testing device, the transfer medium including:
a support; and
a solid-phase reagent layer provided over the support,
wherein the solid-phase reagent layer is a porous body formed of a hydrophobic material, and
wherein a reagent reactive with a sample is formed as a solid phase over a surface of the solid-phase reagent layer opposite to a surface of the solid-phase reagent layer facing the support and inside voids of the solid-phase reagent layer.
<16> The transfer medium for a testing device according to <15>,
wherein the material constituting the solid-phase reagent layer has a contact angle of 75 degrees or greater with respect to distilled water at 25 degrees C.
<17> The transfer medium for a testing device according to <15> or <16>,
wherein voidage of the solid-phase reagent layer before formation of the reagent as the solid phase is 10% or higher but 45% or lower.
<18> The transfer medium for a testing device according to any one of <15> to <17>, the transfer medium further including
a release layer between the support and the solid-phase reagent layer.

<19> The transfer medium for a testing device according to any one of <15> to <18>,
wherein the solid-phase reagent layer is a release and solid-phase reagent layer that serves also as a release layer.
<20> A method for producing a testing device, the method including
a step of bringing the solid-phase reagent layer of the transfer medium for a testing device according to any one of <15> to <19> into contact with a flow path member to transfer the solid-phase reagent layer onto the flow path member.
<21> A testing method including:
a step of supplying a sample to the flow path member of the testing device according to any one of <1> to <13>; and
a step of bringing the reagent formed as the solid phase over the resin layer into contact with the sample to release the reagent from the resin layer.
<22> The testing method according to <21>, further including a step of making the reagent formed as the solid phase over the resin layer capture a portion of the sample.

The testing device according to any one of <1> to <13>, the testing kit according to <14>, the transfer medium for a testing device according to any one of <15> to <19>, the method for producing a testing device according to <20>, and the testing method according to <21> or <22> can solve the various problems in the related art and can achieve the object of the present disclosure.

What is claimed is:

1. A testing device comprising:
    a porous flow path member in which a flow path for flowing a sample is formed; and
    a resin layer provided at at least one position over the flow path member,
    wherein the resin layer comprises a porous body formed of a hydrophobic material, and
    wherein a reagent reactive with the sample is formed as a solid phase over a surface of the resin layer facing the flow path member and inside voids of the resin layer,
    wherein the resin layer comprises a first resin layer and a second resin layer that are provided over the flow path member,
    wherein
    the first resin layer comprises the porous body comprising the hydrophobic material,
    the first resin layer comprises at least a capture antibody as the reagent reactive with the sample over a surface of the first resin layer facing the flow path member and inside voids of the first resin layer, and
    the second resin layer comprises a labeled antibody over a surface of the second resin layer facing the flow path member.

2. The testing device according to claim 1,
wherein the resin layer comprises a water-insoluble resin.

3. The testing device according to claim 1,
wherein the first resin layer comprises a plurality of first resin layers.

4. The testing device according to claim 1,
wherein the first resin layer comprises a resin that comprises a hydrophobic group.

5. The testing device according to claim 4,
wherein the resin that comprises a hydrophobic group comprises any one of a hydrophobic resin and a first amphiphilic resin.

6. The testing device according to claim 1,
wherein the second resin layer comprises a second amphiphilic resin.

7. The testing device according to claim 6,
wherein the first amphiphilic resin comprises a resin that comprises more hydrophobic groups than the second amphiphilic resin comprises.

8. A testing kit comprising:
    the testing device according to claim 1; and
    at least one selected from the group consisting of a sample picking unit configured to pick a sample and a liquid for treating the sample.

9. A testing method with a testing device according to claim 1, the testing method comprising:
    supplying the sample to the flow path member; and
    bringing the reagent formed as the solid phase over the resin layer into contact with the sample to release the reagent from the resin layer.

10. The testing method according to claim 9, further comprising:
    making the reagent formed as the solid phase over the resin layer capture a portion of the sample.

* * * * *